(12) United States Patent
Yang et al.

(10) Patent No.: US 12,201,473 B2
(45) Date of Patent: Jan. 21, 2025

(54) SYSTEMS, DEVICES, AND METHODS FOR REDUCING REVERBERATION SIGNALS IN INTRAVASCULAR ULTRASOUND IMAGING

(71) Applicant: PHILIPS IMAGE GUIDED THERAPY CORPORATION, San Diego, CA (US)

(72) Inventors: Yiqun Yang, Sacramento, CA (US); Andrew Hancock, Sacramento, CA (US); David Hope Simpson, Bothell, WA (US)

(73) Assignee: PHILIPS IMAGE GUIDED THERAPY CORPORATION, San Diego, CA (US)

( * ) Notice: Subject to any disclaimer, the term of this patent is extended or adjusted under 35 U.S.C. 154(b) by 112 days.

(21) Appl. No.: 18/084,687

(22) Filed: Dec. 20, 2022

(65) Prior Publication Data

US 2023/0190230 A1 Jun. 22, 2023

Related U.S. Application Data

(60) Provisional application No. 63/292,487, filed on Dec. 22, 2021.

(51) Int. Cl.
*A61B 8/12* (2006.01)
*A61B 8/08* (2006.01)

(52) U.S. Cl.
CPC .............. *A61B 8/12* (2013.01); *A61B 8/5207* (2013.01)

(58) Field of Classification Search
CPC .......... A61B 8/12; A61B 8/5207; A61B 8/54; A61B 8/4488; A61B 8/4494; G01S 7/52077; G01S 7/52026; G01S 15/8927
See application file for complete search history.

(56) References Cited

U.S. PATENT DOCUMENTS

| | | | |
|---|---|---|---|
| 6,200,268 B1 | 3/2001 | Vince | |
| 6,381,350 B1 | 4/2002 | Klingensmith | |
| 6,776,763 B2 | 8/2004 | Nix | |
| 7,074,188 B2 | 7/2006 | Nair | |
| 7,175,597 B2 | 2/2007 | Vince | |
| 7,226,417 B1 | 6/2007 | Eberle | |
| 7,846,101 B2 | 12/2010 | Eberle | |
| 11,413,017 B2 | 8/2022 | Stigall | |
| 2020/0214663 A1* | 7/2020 | Shin | A61B 8/5246 |

* cited by examiner

*Primary Examiner* — Boniface N Nganga

(57) ABSTRACT

An intravascular ultrasound (IVUS) imaging system includes an IVUS imaging device positionable within a blood vessel. The IVUS imaging device includes a circumferential array of acoustic elements. The system includes a processor circuit. The processor circuit controls the circumferential array to emit ultrasound pulses. The ultrasound pulses include a first pulse emitted by a first subset of the circumferential array and a second pulse emitted by a second subset of the circumferential array. The second pulse occurs immediately after the first pulse. The first subset and the second subset are circumferentially spaced from one another around the circumferential array. The second subset is outside of a line of sight of first ultrasound echoes associated with the first ultrasound pulse. The processor circuit generates an IVUS image based on the ultrasound pulses and outputs the IVUS image to a display.

13 Claims, 17 Drawing Sheets

SYSTEMS, DEVICES, AND METHODS FOR REDUCING REVERBERATION SIGNALS IN INTRAVASCULAR ULTRASOUND IMAGING

TECHNICAL FIELD

The present disclosure relates generally to intraluminal medical imaging, such as intravascular ultrasound (IVUS) imaging. In particular, ultrasound transducers consecutively emitting ultrasound pulses may be spaced around a circumferential array to reduce artifacts caused by reverberation from previous pulses.

BACKGROUND

Intravascular ultrasound (IVUS) imaging is widely used in interventional cardiology as a diagnostic tool for assessing a diseased vessel, such as an artery, within the human body to determine the need for treatment, to guide the intervention, or to assess its effectiveness. An IVUS device including one or more ultrasound transducers is passed into the vessel and guided to the area to be imaged. The transducers emit ultrasonic energy. Ultrasonic waves are partially reflected by discontinuities in tissue structures (such as various layers of the vessel wall), red blood cells, and other features of interest. Echoes from the reflected waves are received by the transducer and passed along to an IVUS imaging system. The imaging system processes the received ultrasound echoes to produce a cross-sectional image of the vessel where the device is placed.

Solid-state (also known as synthetic-aperture) IVUS catheters are one of the two types of IVUS devices commonly used today, the other type being the rotational IVUS catheter. Solid-state IVUS catheters carry a scanner assembly that includes an array of ultrasound transducers distributed around its circumference along with one or more integrated circuit controller chips mounted adjacent to the transducer array. The controllers select acoustic elements (or groups of elements) for transmitting an ultrasound pulse and for receiving the ultrasound echo signal. By stepping through a sequence of transmit-receive pairs, the solid-state IVUS system can synthesize the effect of a mechanically scanned ultrasound transducer but without moving parts (hence the solid-state designation).

In a solid-state IVUS catheter, typically the sequence of selected transmit-receive pairs follows the order of transducers as they are positioned around the catheter circumference. As a result, after one transducer emits an ultrasound pulse and the echo is received, either the same or the adjacent transducer then emits an ultrasound pulse. Because the time between ultrasound pulses is extremely short (i.e., as short as 18.6 μs), one pulse may not completely die out before the next pulse is emitted. Because the transducers receiving ultrasound echoes are typically close to one another, a receiving transducer may detect an ultrasound echo from one ultrasound pulse as well as left over reverberation from a previous ultrasound pulse. These left over reverberations detected by the receiving transducers cause artifacts or "false targets" to appear in the resulting IVUS image. Such artifacts may appear in the image as structures in the patient anatomy which are not actually there. These artifacts can be difficult for a physician to distinguish from actual structures in the IVUS image.

SUMMARY

Embodiments of the present disclosure are intraluminal imaging devices, systems, and methods for reducing reverberation signals received by ultrasound transducers during an IVUS imaging procedure. Specifically, a processor circuit may control a circumferential array of ultrasound transducers positioned on an imaging assembly. The processor circuit directs a transducer to emit an ultrasound pulse. The processor circuit then directs a different transducer spaced from the original transducer to emit an additional ultrasound pulse. After this second pulse, the processor circuit may direct these transducers spaced apart from one another to continue alternating emitting ultrasound pulses or may direct other transducers to emit ultrasound pulses in a similar alternating pattern. By spacing the positions of consecutively emitting transducers, the amount of reverberation signals detected by receiving ultrasound transducers can be significantly reduced. This is because after one transducer emits a pulse, as another pulse is emitted at a removed location, the original pulse has more time to die out before the transducer emits an additional pulse. This increased time between ultrasound pulses ensures that one ultrasound pulse has completely died out in the local region around a receiving transducer before another pulse is emitted. Various time intervals between ultrasound pulses may be implemented to further reduce reverberation signals. In addition, consecutively emitting transducers may be spaced from each other according to various angles and/or sequences around the circumference of an imaging assembly with varying effects on reverberation signal reduction.

According to an exemplary aspect, an intravascular ultrasound (IVUS) imaging system is provided. The system includes an IVUS imaging device configured to be positioned within a blood vessel of a patient, wherein the IVUS imaging device comprises a circumferential array of acoustic elements; a processor circuit in communication with the IVUS imaging device, wherein the processor circuit is configured to: control the circumferential array to emit a plurality of ultrasound pulses, wherein the plurality of ultrasound pulses comprises: a first ultrasound pulse emitted by a first subset of the circumferential array; and a second ultrasound pulse emitted by a second subset of the circumferential array, wherein the second ultrasound pulse occurs immediately after the first ultrasound pulse in a succession of the plurality of ultrasound pulses, wherein the first subset and the second subset are circumferentially spaced from one another around the circumferential array, and wherein the second subset is outside of a line of sight of first ultrasound echoes associated with the first ultrasound pulse; generate an IVUS image based on the plurality of ultrasound pulses; and output the IVUS image to a display in communication with the processor circuit.

In some aspects, the first ultrasound pulse is associated with a first aperture of the circumferential array, and the second ultrasound pulse is associated with a second aperture of the circumferential array. In some aspects, the first subset comprises a single acoustic element of the circumferential array, and the second subset comprises a different, single acoustic element of the circumferential array. In some aspects, the first subset comprises a first plurality of acoustic elements of the circumferential array, and the second subset comprises a second plurality of acoustic elements of the circumferential array. In some aspects, the processor circuit is configured to control the circumferential array to: receive the first ultrasound echoes; and receive second ultrasound echoes associated with the second ultrasound pulse; and the processor circuit is configured to generate the IVUS image based on ultrasound data representative of the first ultrasound echoes and the second ultrasound echoes. In some aspects, the processor circuit is configured to control the circumferential array to receive the first ultrasound echoes using a third subset of the circumferential array, the processor circuit is configured to control the circumferential array to receive the second ultrasound echoes using a fourth subset of the circumferential array, the third subset is within the line of sight of the first ultrasound echoes, and the fourth subset is within the line of sight of the second ultrasound echoes. In some aspects, the first subset and the third subset are identical, and the second subset and the fourth subset are identical. In some aspects, the first subset and the second subset are circumferentially spaced from one another by a first portion of the circumferential array, the first subset and the third subset are circumferentially spaced from one another by a second portion of the circumferential array that is smaller than the first portion, the second subset and the fourth subset are circumferentially spaced from one another by a third portion of the circumferential array that is smaller than the first portion. In some aspects, the first subset and the second subset are symmetrically spaced from one another around the circumferential array. In some aspects, the plurality of ultrasound pulses comprises a third ultrasound pulse emitted by a third subset of the circumferential array, the third ultrasound pulse occurs immediately after the second ultrasound pulse in the succession of the plurality of ultrasound pulses, and the first subset, the second subset, and the third subset are circumferentially spaced from one another around the circumferential array, and the third subset is outside of the line of sight of the first ultrasound echoes associated with the first ultrasound pulse and second ultrasound echoes associated with the second ultrasound pulse. In some aspects, the first subset and the second subset are symmetrically spaced from one another around the circumferential array. In some aspects, the IVUS imaging device comprises a plurality of communication lines in communication with the circumferential array of acoustic elements, the plurality of communication lines comprises a first data channel and a second data channel, the plurality of ultrasound pulses comprises: a third ultrasound pulse emitted by a third subset of the circumferential array; and a fourth ultrasound pulse emitted by a fourth subset of the circumferential array, the processor circuit is configured to control the circumferential array to emit the first ultrasound pulse and the third ultrasound pulse simultaneously, the first ultrasound pulse is associated with the first data channel and the third ultrasound pulse is associated with the second data channel, the processor circuit is configured to control the circumferential array to emit the second ultrasound pulse and the fourth ultrasound pulse simultaneously, the third ultrasound pulse is associated with the first data channel and the fourth ultrasound pulse is associated with the second data channel. In some aspects, the plurality of ultrasound pulses comprises: an additional first ultrasound pulse occurring immediately after the first ultrasound pulse in the succession of the plurality of ultrasound pulses; and an additional second ultrasound pulse occurring immediately after the second ultrasound pulse in the succession of the plurality of ultrasound pulses.

According to an exemplary aspect, an intravascular ultrasound (IVUS) imaging system is provided. The system includes an IVUS imaging catheter configured to be positioned within a blood vessel of a patient, wherein the IVUS imaging catheter comprises a circumferential array of acoustic elements; and a processor circuit in communication with the IVUS imaging catheter, wherein the processor circuit is configured to: control the circumferential array to obtain IVUS imaging data, wherein the IVUS imaging data is representative of: a first transmit-receive aperture comprising a first combined radiation pattern and associated with at least one first acoustic element of the circumferential array; and a second transmit-receive aperture comprising a second combined radiation pattern and associated with at least one second acoustic element of the circumferential array, wherein the IVUS imaging data representative of the second transmit-receive aperture is obtained immediately after the IVUS imaging data representative of the first transmit-receive aperture, and wherein the at least one first acoustic element and the at least one second acoustic element are circumferentially spaced from one another around the circumferential array such that the first combined radiation pattern and the second combined radiation pattern are non-overlapping or minimally overlapping; generate an IVUS image based on the IVUS imaging data; and output the IVUS image to a display in communication with the processor circuit.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which.

DETAILED DESCRIPTION

Figure 1:
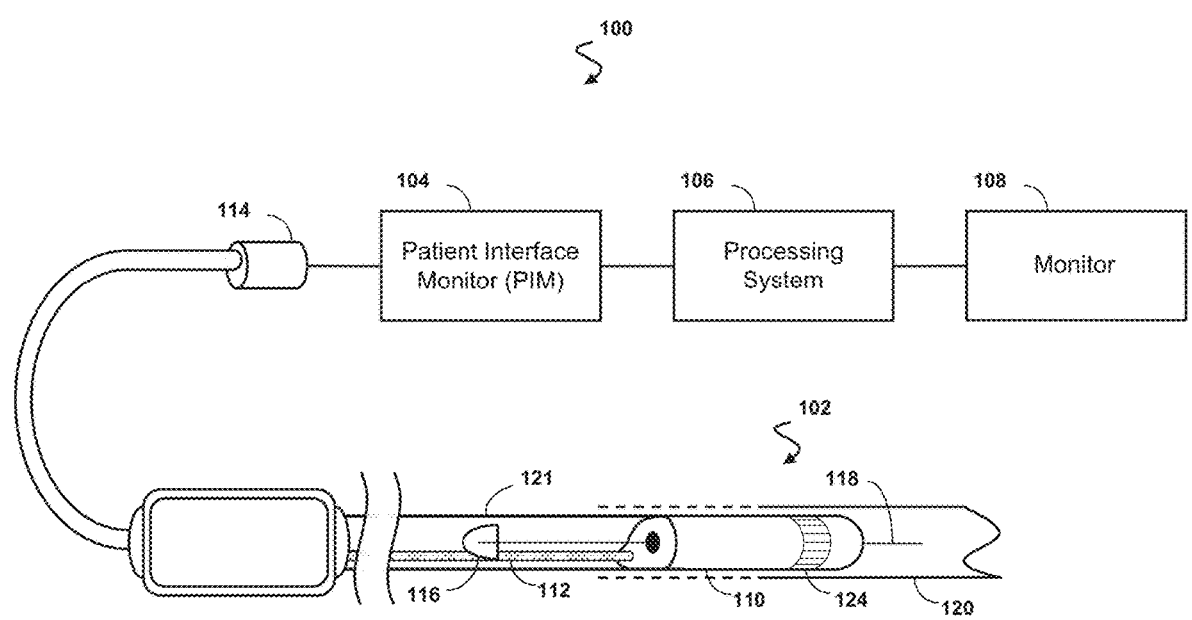
FIG. 1 is a schematic diagram of an intraluminal imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. For example, while the focusing system is described in terms of cardiovascular imaging, it is understood that it is not intended to be limited to this application. The system is equally well suited to any application requiring imaging within a confined cavity. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

FIG. 1 is a schematic diagram of an intraluminal imaging system 100, according to aspects of the present disclosure. The intraluminal imaging system 100 can be an ultrasound imaging system. In some instances, the system 100 can be an intravascular ultrasound (IVUS) imaging system. The system 100 may include an intraluminal imaging device 102 such as a catheter, guide wire, or guide catheter, a patient interface module (PIM) 104, a processing system or console 106, and a monitor 108. The intraluminal imaging device 102 can be an ultrasound imaging device. In some instances, the device 102 can be an IVUS imaging device, such as a solid-state IVUS device.

At a high level, the IVUS device 102 emits ultrasonic energy from a transducer array 124 included in scanner assembly 110, also referred to as an IVUS imaging assembly, mounted near a distal end of the catheter device. The ultrasonic energy is reflected by tissue structures in the surrounding medium, such as a vessel 120, or another body lumen surrounding the scanner assembly 110, and the ultrasound echo signals are received by the transducer array 124. In that regard, the device 102 can be sized, shaped, or otherwise configured to be positioned within the body lumen of a patient. The PIM 104 transfers the received echo signals to the console or computer 106 where the ultrasound image (including flow information in some embodiments) is reconstructed and displayed on the monitor 108. The console or computer 106 can include a processor and a memory. The computer or computing device 106 can be operable to facilitate the features of the IVUS imaging system 100 described herein. For example, the processor can execute computer readable instructions stored on the non-transitory tangible computer readable medium.

The PIM 104 facilitates communication of signals between the IVUS console 106 and the scanner assembly 110 included in the IVUS device 102. This communication includes the steps of: (1) providing commands to integrated circuit controller chip(s) 206A and 206B, illustrated in FIG. 2, included in the scanner assembly 110 to select the particular transducer array element(s), or acoustic element(s), to be used for transmit and receive, (2) providing the transmit trigger signals to the integrated circuit controller chip(s) 206A and 206B (FIG. 2) included in the scanner assembly 110 to activate the transmitter circuitry to generate an electrical pulse to excite the selected transducer array element(s), and/or (3) accepting amplified echo signals received from the selected transducer array element(s) via amplifiers included on the integrated circuit controller chip(s) 126 of the scanner assembly 110. In some embodiments, the PIM 104 performs preliminary processing of the echo data prior to relaying the data to the console 106. In examples of such embodiments, the PIM 104 performs amplification, filtering, and/or aggregating of the data. In an embodiment, the PIM 104 also supplies high- and low-voltage DC power to support operation of the device 102 including circuitry within the scanner assembly 110.

The IVUS console 106 receives the echo data from the scanner assembly 110 by way of the PIM 104 and processes the data to reconstruct an image of the tissue structures in the medium surrounding the scanner assembly 110. The console 106 outputs image data such that an image of the vessel 120, such as a cross-sectional image of the vessel 120, is displayed on the monitor 108. The vessel 120 may represent fluid filled or surrounded structures, both natural and man-made. The vessel 120 may be within a body of a patient. The vessel 120 may be a blood vessel, such as an artery or a vein of a patient's vascular system, including cardiac vasculature, peripheral vasculature, neural vasculature, renal vasculature, and/or any other suitable lumen inside the body. For example, the device 102 may be used to examine any number of anatomical locations and tissue types, including without limitation, organs including the liver, heart, kidneys, gall bladder, pancreas, lungs; ducts; intestines; nervous system structures including the brain, dural sac, spinal cord and peripheral nerves; the urinary tract; as well as valves within the blood, chambers or other parts of the heart, and/or other systems of the body. In addition to natural structures, the device 102 may be used to examine man-made structures such as, but without limitation, heart valves, stents, shunts, filters and other devices.

Figure 2:
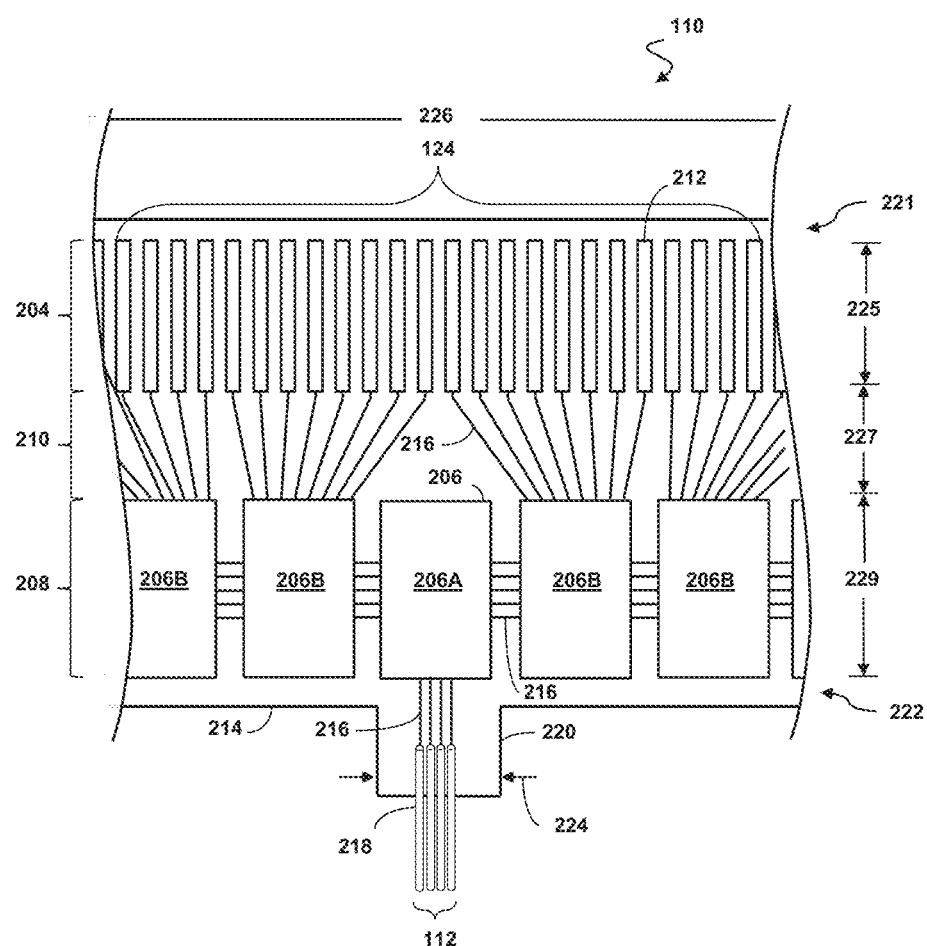
FIG. 2 is a diagrammatic top view of an ultrasound imaging assembly in a flat configuration, according to aspects of the present disclosure.

In some embodiments, the IVUS device includes some features similar to traditional solid-state IVUS catheters, such as the EagleEye® catheter available from Volcano Corporation and those disclosed in U.S. Pat. No. 7,846,101 hereby incorporated by reference in its entirety. For example, the IVUS device 102 includes the scanner assembly 110 near a distal end of the device 102 and a transmission line bundle 112 extending along the longitudinal body of the device 102. The transmission line bundle or cable 112 can include a plurality of conductors, including one, two, three, four, five, six, seven, or more conductors 218 (FIG. 2). It is understood that any suitable gauge wire can be used for the conductors 218. In an embodiment, the cable 112 can include a four-conductor transmission line arrangement with, e.g., 41 AWG gauge wires. In an embodiment, the cable 112 can include a seven-conductor transmission line arrangement utilizing, e.g., 44 AWG gauge wires. In some embodiments, 43 AWG gauge wires can be used.

The transmission line bundle 112 terminates in a PIM connector 114 at a proximal end of the device 102. The PIM connector 114 electrically couples the transmission line bundle 112 to the PIM 104 and physically couples the IVUS device 102 to the PIM 104. In an embodiment, the IVUS device 102 further includes a guide wire exit port 116. Accordingly, in some instances the IVUS device is a rapid-exchange catheter. The guide wire exit port 116 allows a guide wire 118 to be inserted towards the distal end in order to direct the device 102 through the vessel 120.

FIG. 2 is a diagrammatic top view of a portion of a flexible assembly 110, according to aspects of the present disclosure. The flexible assembly 110 includes a transducer array 124 formed in a transducer region 204 and transducer control logic dies 206 (including dies 206A and 206B) formed in a control region 208, with a transition region 210 disposed therebetween. The transducer array 124 includes an array of ultrasound transducer elements 212 housing transducer elements 512 (shown in FIG. 5). The transducer control logic dies 206 are mounted on a flexible substrate 214 into which the transducer elements 212 have been previously integrated. The flexible substrate 214 is shown in a flat configuration in FIG. 2. Though six control logic dies 206 are shown in FIG. 2, any number of control logic dies 206 may be used. For example, one, two, three, four, five, six, seven, eight, nine, ten, or more control logic dies 206 may be used.

The flexible substrate 214, on which the transducer control logic dies 206 and the transducer elements 212 are mounted, provides structural support and interconnects for electrical coupling. The flexible substrate 214 may be constructed to include a film layer of a flexible polyimide material such as KAPTON™ (trademark of DuPont). Other suitable materials include polyester films, polyimide films, polyethylene napthalate films, or polyetherimide films, liquid crystal polymer, other flexible printed semiconductor substrates as well as products such as Upilex® (registered trademark of Ube Industries) and TEFLON® (registered trademark of E.I. du Pont). In the flat configuration illustrated in FIG. 2, the flexible substrate 214 has a generally rectangular shape. As shown and described herein, the flexible substrate 214 is configured to be wrapped around a support member 230 (FIG. 3) in some instances. Therefore, the thickness of the film layer of the flexible substrate 214 is generally related to the degree of curvature in the final assembled flexible assembly 110. In some embodiments, the film layer is between 5 μm and 100 μm, with some particular embodiments being between 5 μm and 25.1 μm, e.g., 6 μm.

The set of transducer control logic dies 206 is a non-limiting example of a control circuit. The transducer region 204 is disposed at a distal portion 221 of the flexible substrate 214. The control region 208 is disposed at a proximal portion 222 of the flexible substrate 214. The transition region 210 is disposed between the control region 208 and the transducer region 204. Dimensions of the transducer region 204, the control region 208, and the transition region 210 (e.g., lengths 225, 227, 229) can vary in different embodiments. In some embodiments, the lengths 225, 227, 229 can be substantially similar or, the length 227 of the transition region 210 may be less than lengths 225 and 229, the length 227 of the transition region 210 can be greater than lengths 225, 229 of the transducer region and controller region, respectively.

The control logic dies 206 are not necessarily homogenous. In some embodiments, a single controller is designated a master control logic die 206A and contains the communication interface for cable 112, between a processing system, e.g., processing system 106, and the flexible assembly 110. Accordingly, the master control circuit may include control logic that decodes control signals received over the cable 112, transmits control responses over the cable 112, amplifies echo signals, and/or transmits the echo signals over the cable 112. The remaining controllers are slave controllers 206B. The slave controllers 206B may include control logic that drives a plurality of transducer elements 512 positioned on a transducer element 212 to emit an ultrasonic signal and selects a transducer element 212 to receive an echo. In the depicted embodiment, the master controller 206A does not directly control any transducer elements 212. In other embodiments, the master controller 206A drives the same number of transducer elements 212 as the slave controllers 206B or drives a reduced set of transducer elements 212 as compared to the slave controllers 206B. In an exemplary embodiment, a single master controller 206A and eight slave controllers 206B are provided with eight transducers assigned to each slave controller 206B.

To electrically interconnect the control logic dies 206 and the transducer elements 212, in an embodiment, the flexible substrate 214 includes conductive traces 216 formed in the film layer that carry signals between the control logic dies 206 and the transducer elements 212. In particular, the conductive traces 216 providing communication between the control logic dies 206 and the transducer elements 212 extend along the flexible substrate 214 within the transition region 210. In some instances, the conductive traces 216 can also facilitate electrical communication between the master controller 206A and the slave controllers 206B. The conductive traces 216 can also provide a set of conductive pads that contact the conductors 218 of cable 112 when the conductors 218 of the cable 112 are mechanically and electrically coupled to the flexible substrate 214. Suitable materials for the conductive traces 216 include copper, gold, aluminum, silver, tantalum, nickel, and tin, and may be deposited on the flexible substrate 214 by processes such as sputtering, plating, and etching. In an embodiment, the flexible substrate 214 includes a chromium adhesion layer. The width and thickness of the conductive traces 216 are selected to provide proper conductivity and resilience when the flexible substrate 214 is rolled. In that regard, an exemplary range for the thickness of a conductive trace 216 and/or conductive pad is between 1-5 µm. For example, in an embodiment, 5 µm conductive traces 216 are separated by 5 µm of space. The width of a conductive trace 216 on the flexible substrate may be further determined by the width of the conductor 218 to be coupled to the trace or pad.

The flexible substrate 214 can include a conductor interface 220 in some embodiments. The conductor interface 220 can be in a location of the flexible substrate 214 where the conductors 218 of the cable 112 are coupled to the flexible substrate 214. For example, the bare conductors of the cable 112 are electrically coupled to the flexible substrate 214 at the conductor interface 220. The conductor interface 220 can be tab extending from the main body of flexible substrate 214. In that regard, the main body of the flexible substrate 214 can refer collectively to the transducer region 204, a controller region 208, and the transition region 210. In the illustrated embodiment, the conductor interface 220 extends from the proximal portion 222 of the flexible substrate 214. In other embodiments, the conductor interface 220 is positioned at other parts of the flexible substrate 214, such as the distal portion 221, or the flexible substrate 214 may lack the conductor interface 220. A value of a dimension of the tab or conductor interface 220, such as a width 224, can be less than the value of a dimension of the main body of the flexible substrate 214, such as a width 226. In some embodiments, the substrate forming the conductor interface 220 is made of the same material(s) and/or is similarly flexible as the flexible substrate 214. In other embodiments, the conductor interface 220 is made of different materials and/or is comparatively more rigid than the flexible substrate 214. For example, the conductor interface 220 can be made of a plastic, thermoplastic, polymer, hard polymer, etc., including polyoxymethylene (e.g., DELRIN®), polyether ether ketone (PEEK), nylon, Liquid Crystal Polymer (LCP), and/or other suitable materials.

Figure 3:
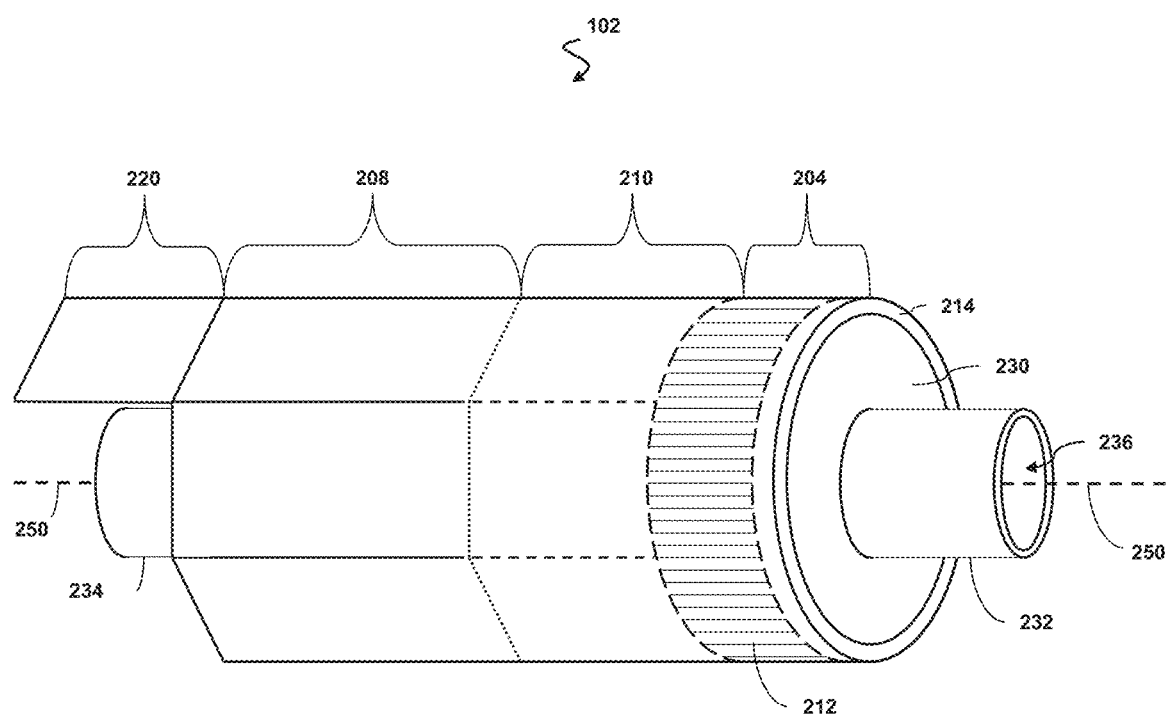
FIG. 3 is a diagrammatic perspective view of the ultrasound imaging assembly shown in FIG. 2 in a rolled configuration around a support member, according to aspects of the present disclosure.

FIG. 3 illustrates a perspective view of the scanner assembly 110 in a rolled configuration. In some instances, the flexible substrate 214 is transitioned from a flat configuration (FIG. 2) to a rolled or more cylindrical configuration (FIG. 3). For example, in some embodiments, techniques are utilized as disclosed in one or more of U.S. Pat. No. 6,776,763, titled "ULTRASONIC TRANSDUCER ARRAY AND METHOD OF MANUFACTURING THE SAME" and U.S. Pat. No. 7,226,417, titled "HIGH RESOLUTION INTRAVASCULAR ULTRASOUND SENSING ASSEMBLY HAVING A FLEXIBLE SUBSTRATE," each of which is hereby incorporated by reference in its entirety.

Depending on the application and embodiment of the presently disclosed invention, transducer elements 212 may be piezoelectric transducers, single crystal transducer, or PZT (lead zirconate titanate) transducers. In other embodiments, the transducer elements of transducer array 124 may be flexural transducers, piezoelectric micromachined ultrasonic transducers (PMUTs), capacitive micromachined ultrasonic transducers (CMUTs), or any other suitable type of transducer element. In such embodiments, transducer elements 212 may comprise an elongate semiconductor material or other suitable material that allows micromachining or similar methods of disposing extremely small elements or circuitry on a substrate.

In some embodiments, the transducer elements 212 and the controllers 206 can be positioned in an annular configuration, such as a circular configuration or in a polygon configuration, around a longitudinal axis 250 of a support member 230. It is understood that the longitudinal axis 250 of the support member 230 may also be referred to as the longitudinal axis of the scanner assembly 110, the flexible elongate member 121, or the device 102. For example, a cross-sectional profile of the imaging assembly 110 at the transducer elements 212 and/or the controllers 206 can be a circle or a polygon. Any suitable annular polygon shape can be implemented, such as one based on the number of controllers or transducers, flexibility of the controllers or transducers, etc. Some examples may include a pentagon, hexagon, heptagon, octagon, nonagon, decagon, etc. In some examples, the transducer controllers 206 may be used for controlling the ultrasound transducers 512 of transducer elements 212 to obtain imaging data associated with the vessel 120.

The support member 230 can be referenced as a unibody in some instances. The support member 230 can be composed of a metallic material, such as stainless steel, or a non-metallic material, such as a plastic or polymer as described in U.S. Provisional Application No. 61/985,220, "Pre-Doped Solid Substrate for Intravascular Devices," filed Apr. 28, 2014, ('220 application) the entirety of which is hereby incorporated by reference herein. In some embodiments, support member 230 may be composed of 303 stainless steel. The support member 230 can be a ferrule having a distal flange or portion 232 and a proximal flange or portion 234. The support member 230 can be tubular in shape and define a lumen 236 extending longitudinally therethrough. The lumen 236 can be sized and shaped to receive the guide wire 118. The support member 230 can be manufactured using any suitable process. For example, the support member 230 can be machined and/or electrochemically machined or laser milled, such as by removing material from a blank to shape the support member 230, or molded, such as by an injection molding process or a micro injection molding process.

Figure 4:
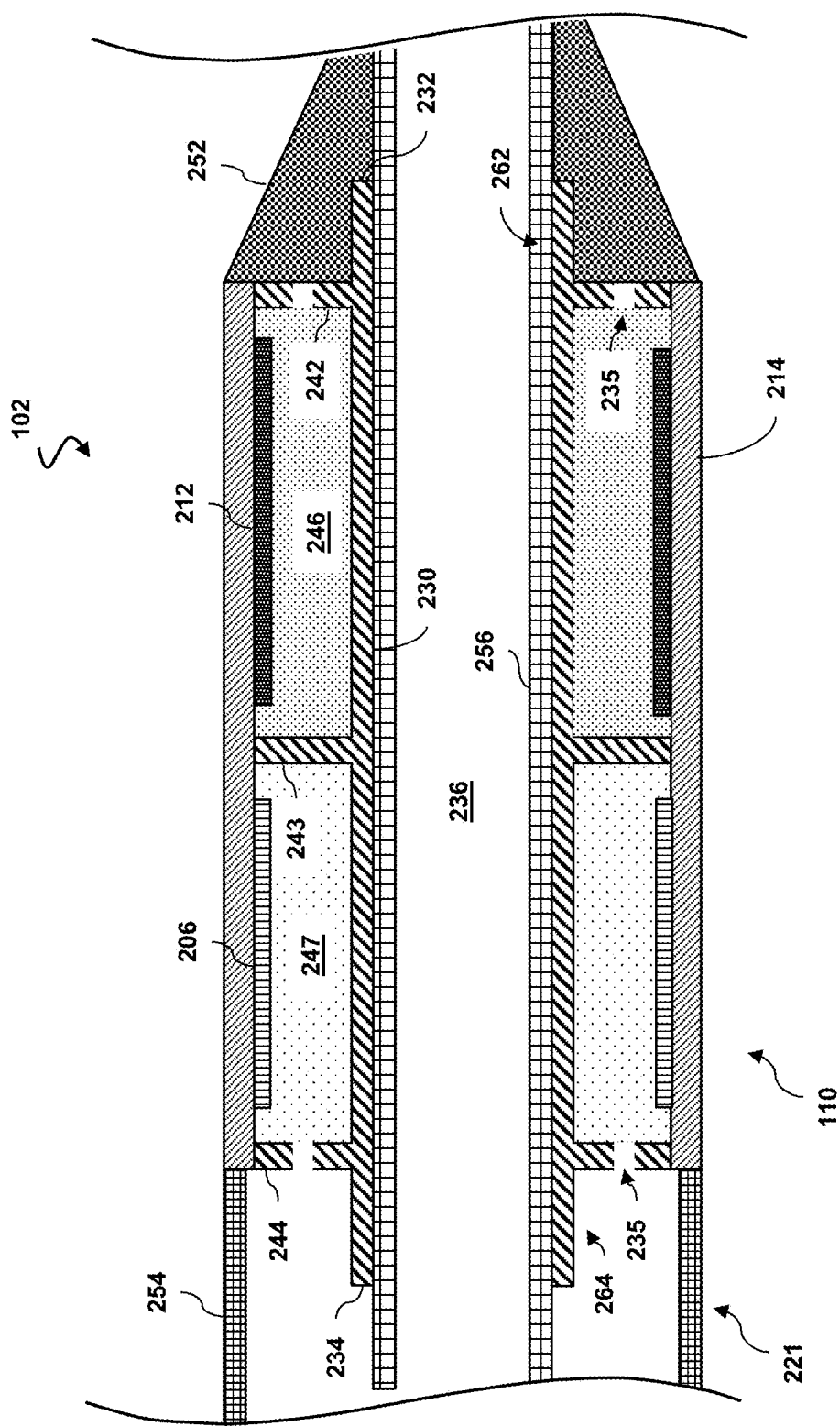
FIG. 4 is a diagrammatic cross-sectional side view of the ultrasound imaging assembly shown in FIG. 3, according to aspects of the present disclosure.

Referring now to FIG. 4, shown therein is a diagrammatic cross-sectional side view of a distal portion of the intraluminal imaging device 102, including the flexible substrate 214 and the support member 230, according to aspects of the present disclosure. The lumen 236 may be connected with the entry/exit port 116 and is sized and shaped to receive the guide wire 118 (FIG. 1). In some embodiments, the support member 230 may be integrally formed as a unitary structure, while in other embodiments the support member 230 may be formed of different components, such as a ferrule and stands 242, 243, and 244, that are fixedly coupled to one another. In some cases, the support member 230 and/or one or more components thereof may be completely integrated with inner member 256. In some cases, the inner member 256 and the support member 230 may be joined as one, e.g., in the case of a polymer support member.

Stands 242, 243, and 244 that extend vertically are provided at the distal, central, and proximal portions respectively, of the support member 230. The stands 242, 243, and 244 elevate and support the distal, central, and proximal portions of the flexible substrate 214. In that regard, portions of the flexible substrate 214, such as the transducer portion 204 (or transducer region 204), can be spaced from a central body portion of the support member 230 extending between the stands 242, 243, and 244. The stands 242, 243, 244 can have the same outer diameter or different outer diameters. For example, the distal stand 242 can have a larger or smaller outer diameter than the central stand 243 and/or proximal stand 244 and can also have special features for rotational alignment as well as control chip placement and connection.

To improve acoustic performance, the cavity between the transducer array 212 and the surface of the support member 230 may be filled with an acoustic backing material 246. The liquid backing material 246 can be introduced between the flexible substrate 214 and the support member 230 via passageway 235 in the stand 242, or through additional recesses as will be discussed in more detail hereafter. The backing material 246 may serve to attenuate ultrasound energy emitted by the transducer array 212 that propagates in the undesired, inward direction.

The cavity between the circuit controller chips 206 and the surface of the support member 230 may be filled with an underfill material 247. The underfill material 247 may be an adhesive material (e.g. an epoxy) which provides structural support for the circuit controller chips 206 and/or the flexible substrate 214. The underfill 247 may additionally be any suitable material.

In some embodiments, the central body portion of the support member can include recesses allowing fluid communication between the lumen of the unibody and the cavities between the flexible substrate 214 and the support member 230. Acoustic backing material 246 and/or underfill material 247 can be introduced via the cavities (during an assembly process, prior to the inner member 256 extending through the lumen of the unibody. In some embodiments, suction can be applied via the passageways 235 of one of the stands 242, 244, or to any other suitable recess while the liquid backing material 246 is fed between the flexible substrate 214 and the support member 230 via the passageways 235 of the other of the stands 242, 244, or any other suitable recess. The backing material can be cured to allow it to solidify and set. In various embodiments, the support member 230 includes more than three stands 242, 243, and 244, only one or two of the stands 242, 243, 244, or none of the stands. In that regard the support member 230 can have an increased diameter distal portion 262 and/or increased diameter proximal portion 264 that is sized and shaped to elevate and support the distal and/or proximal portions of the flexible substrate 214.

The support member 230 can be substantially cylindrical in some embodiments. Other shapes of the support member 230 are also contemplated including geometrical, non-geometrical, symmetrical, non-symmetrical, cross-sectional profiles. As the term is used herein, the shape of the support member 230 may reference a cross-sectional profile of the support member 230. Different portions of the support member 230 can be variously shaped in other embodiments. For example, the proximal portion 264 can have a larger outer diameter than the outer diameters of the distal portion 262 or a central portion extending between the distal and proximal portions 262, 264. In some embodiments, an inner diameter of the support member 230 (e.g., the diameter of the lumen 236) can correspondingly increase or decrease as the outer diameter changes. In other embodiments, the inner diameter of the support member 230 remains the same despite variations in the outer diameter.

A proximal inner member 256 and a proximal outer member 254 are coupled to the proximal portion 264 of the support member 230. The proximal inner member 256 and/or the proximal outer member 254 can comprise a flexible elongate member. The proximal inner member 256 can be received within a proximal flange 234. The proximal outer member 254 abuts and is in contact with the proximal end of flexible substrate 214. A distal tip member 252 is coupled to the distal portion 262 of the support member 230. For example, the distal member 252 is positioned around the distal flange 232. The tip member 252 can abut and be in contact with the distal end of flexible substrate 214 and the stand 242. In other embodiments, the proximal end of the tip member 252 may be received within the distal end of the flexible substrate 214 in its rolled configuration. In some embodiments there may be a gap between the flexible substrate 214 and the tip member 252. The distal member 252 can be the distal-most component of the intraluminal imaging device 102. The distal tip member 252 may be a flexible, polymeric component that defines the distal-most end of the imaging device 102. The distal tip member 252 may additionally define a lumen in communication with the lumen 236 defined by support member 230. The guide wire 118 may extend through lumen 236 as well as the lumen defined by the tip member 252.

One or more adhesives can be disposed between various components at the distal portion of the intraluminal imaging device 102. For example, one or more of the flexible substrate 214, the support member 230, the distal member 252, the proximal inner member 256, the transducer array 212, and/or the proximal outer member 254 can be coupled to one another via an adhesive. Stated differently, the adhesive can be in contact with e.g. the transducer array 212, the flexible substrate 214, the support member 230, the distal member 252, the proximal inner member 256, and/or the proximal outer member 254, among other components.

Figure 5:
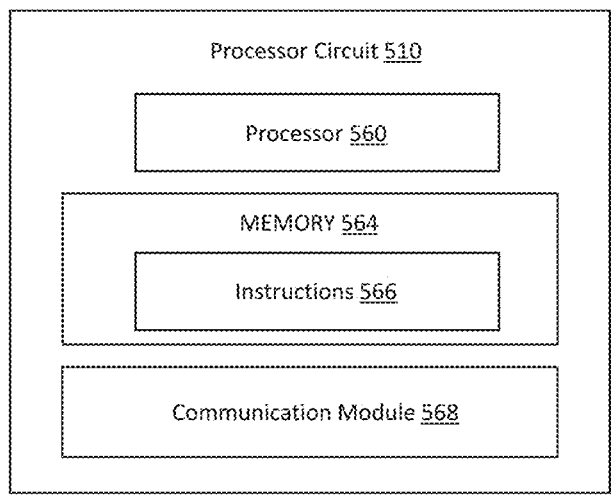
FIG. 5 is a schematic diagram of a processor circuit, according to aspects of the present disclosure.

FIG. 5 is a schematic diagram of a processor circuit, according to aspects of the present disclosure. The processor circuit 510 may be implemented in the control system 130 of FIG. 1, the intraluminal imaging system 101, and/or the x-ray imaging system 151, or any other suitable location. In an example, the processor circuit 510 may be in communication with intraluminal imaging device 102, the x-ray imaging device 152, the display 132 within the system 100. The processor circuit 510 may include the processor 134 and/or the communication interface 140 (FIG. 1). One or more processor circuits 510 are configured to execute the operations described herein. As shown, the processor circuit 510 may include a processor 560, a memory 564, and a communication module 568. These elements may be in direct or indirect communication with each other, for example via one or more buses.

The processor 560 may include a CPU, a GPU, a DSP, an application-specific integrated circuit (ASIC), a controller, an FPGA, another hardware device, a firmware device, or any combination thereof configured to perform the operations described herein. The processor 560 may also be implemented as a combination of computing devices, e.g., a combination of a DSP and a microprocessor, a plurality of microprocessors, one or more microprocessors in conjunction with a DSP core, or any other such configuration.

The memory 564 may include a cache memory (e.g., a cache memory of the processor 560), random access memory (RAM), magnetoresistive RAM (MRAM), read-only memory (ROM), programmable read-only memory (PROM), erasable programmable read only memory (EPROM), electrically erasable programmable read only memory (EEPROM), flash memory, solid state memory device, hard disk drives, other forms of volatile and non-volatile memory, or a combination of different types of memory. In an embodiment, the memory 564 includes a non-transitory computer-readable medium. The memory 564 may store instructions 566. The instructions 566 may include instructions that, when executed by the processor 560, cause the processor 560 to perform the operations described herein with reference to the probe 110 and/or the host 130 (FIG. 1). Instructions 566 may also be referred to as code. The terms "instructions" and "code" should be interpreted broadly to include any type of computer-readable statement(s). For example, the terms "instructions" and "code" may refer to one or more programs, routines, subroutines, functions, procedures, etc. "Instructions" and "code" may include a single computer-readable statement or many computer-readable statements.

The communication module 568 can include any electronic circuitry and/or logic circuitry to facilitate direct or indirect communication of data between the processor circuit 510, the probe 110, and/or the display 132 and/or display 132. In that regard, the communication module 568 can be an input/output (I/O) device. In some instances, the communication module 568 facilitates direct or indirect communication between various elements of the processor circuit 510 and/or the probe 110 (FIG. 1) and/or the host 130 (FIG. 1).

Figure 6:
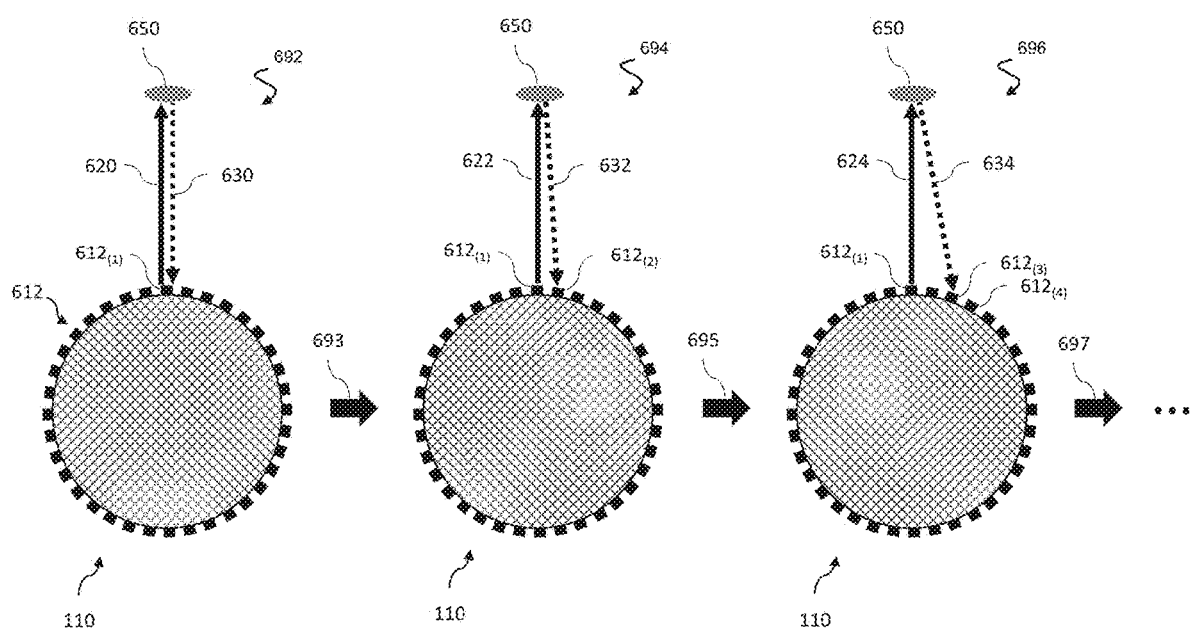
FIG. 6 is a diagrammatic cross-sectional view of the ultrasound imaging assembly illustrating paths of transmitted and received ultrasound pulses over time, according to aspects of the present disclosure.

FIG. 6 is a diagrammatic cross-sectional view of the ultrasound imaging assembly 110 illustrating paths of transmitted and received ultrasound pulses over time, according to aspects of the present disclosure. FIG. 6 includes several depictions of the ultrasound imaging assembly 110 as ultrasound imaging data is obtained during an imaging procedure.

As shown in FIG. 6, multiple ultrasound transducers 612 are positioned in a circumference around the surface of the ultrasound imaging assembly 110. As previously described each of these ultrasound transducers 612 may be configured to transmit ultrasonic energy into a surrounding anatomy and receive reflections from various structures within the anatomy. For example, the processor circuit 510 (FIG. 5) may be configured to control the circumferential array of ultrasound transducers 612 to emit multiple ultrasound pulses.

As shown in FIG. 6, at a time 692, the ultrasound imaging assembly 110 may excite an ultrasound transducer $612_{(1)}$ positioned on the outer surface of the assembly 110. As the transducer $612_{(1)}$ is excited or as a membrane of the transducer $612_{(1)}$ moves in response to receiving an electrical signal, an ultrasound pulse 620 may be transmitted into the surrounding anatomy. The pulse 620 may propagate through the anatomy and reflect off a structure 650 within the anatomy. The reflection 630, may propagate back towards the ultrasound imaging assembly 110. In response to a command from the processor circuit 510, the ultrasound imaging assembly 110 may receive the reflection 630 with the same transducer $612_{(1)}$, as shown in FIG. 6.

In some embodiments, immediately after the ultrasound transducer $612_{(1)}$ transmits an ultrasound pulse and receives any reflections, the ultrasound system 100 may repeat the same process described again. For example, the ultrasound transducer $612_{(1)}$ may emit an ultrasound pulse and the same transducer $612_{(1)}$ may receive a reflection of the pulse. The process of repeating the same transmitting and receiving procedure more than one time in succession may be referred to as accumulation.

The arrows 693 and 695 illustrated between the depictions of the ultrasound imaging assembly 110 in FIG. 6 signify a chronological progression. For example, at a time 692, the transducer $612_{(1)}$ may emit an ultrasound pulse 620 and receive the reflection 630. A period of time may then pass after time 692, as shown by the arrow 693. At time 694, the transducer $612_{(1)}$ may emit an additional ultrasound pulse 622. The pulse 622 may propagate through the surrounding medium and reflect off the structure 650. The ultrasound imaging assembly 110 may then select the transducer $612_{(2)}$, positioned adjacent to the transducer $612_{(1)}$, to receive the resulting reflection 632. A shown by the arrow 695, an additional period of time may then elapse and at time 696, the transducer $612_{(1)}$ may emit another ultrasound pulse 624. The pulse 624 may propagate through the anatomy and reflect off the structure 650. The imaging assembly 110 may select the transducer $612_{(3)}$, adjacent to the transducer $612_{(2)}$, to receive the reflection 634.

As illustrated by the arrow 697, an additional period of time may elapse, and the process may continue in a similar manner. For example, the transducer $612_{(1)}$ may emit additional ultrasound pulses and the imaging assembly 110 may walk through the neighboring transducers in turn to receive reflections. For example, after the time period 697, the transducer $612_{(4)}$ may receive a reflection of a pulse emitted by the transducer $612_{(1)}$, followed by the transducers $612_{(5)}$, $612_{(6)}$, and so on.

In some embodiments, the processor circuit 510 (FIG. 5) of the system 100 may determine which transducers 612 will be selected to receive reflections based on the characteristics of the emitted ultrasound pulse. For example, as will be described in more detail with reference to FIG. 8, an emitted ultrasound pulse may propagate from a transmitting transducer according to a radiation pattern. The radiation pattern may depend on the size and shape of the transducer and the frequency of the ultrasound pulse, among other contributing factors. A receiving transducer may receive reflections according to a similar radiation pattern. The receiving radiation pattern may also depend on the size and shape of the receiving transducer as well as the frequency of reflections received. In some embodiments, the processor circuit 510 (FIG. 5) may determine the number of allowable transducers along the circumference between a transmitting and a receiving transducer based on the radiation patterns of the transmitting and receiving transducers. For example, the processor circuit 510 may specify that a transducer act as a receiving transducer for a chosen transmitting transducer if the structure 650 being imaged lies within the radiation pattern of both the transmitting transducer and the receiving transducer. In some embodiments, all transducers with radiation patterns which overlap with the radiation pattern of the transmitting transducer may be selected as receiving transducers and may iteratively be chosen to receive reflections from an emitted pulse in turn, as described with reference to FIG. 6.

In the example shown in FIG. 6, after all receiving transducers have received reflections from the ultrasound pulse emitted by the transducer $612_{(1)}$, the same process may be repeated with transducer $612_{(2)}$ acting as the transmitting transducer. Specifically, transducer $612_{(2)}$ may emit an ultrasound pulse. The same transducer $612_{(2)}$ may receive any reflections. Then, transducer $612_{(2)}$ may emit another ultrasound pulse and transducer $612_{(3)}$ may receive reflections, and so on. This sequence may be followed until each transducer 612 has acted as the transmitting transducer and all corresponding receiving transducer has received reflections. The acquired data may then be processed to generate and display an intravascular ultrasound (IVUS) image.

As described in FIG. 6, the intravascular ultrasound imaging system includes an IVUS imaging device configured to be positioned within a blood vessel of a patient and the IVUS imaging device includes a circumferential array of acoustic elements. The processor circuit 510 (FIG. 5) is configured to control the circumferential array to emit and/or receive multiple ultrasound pulses.

A transmitting transducer, such as transducer $612_{(1)}$ at time 694, and a receiving transducer, such as transducer $612_{(2)}$ at time 694, intended to transmit an ultrasound pulse and receive a resulting reflection respectively may be referred to as a transmit-receive pair. The sequence of the transmitting a pulse with the transmitting transducer and subsequently receiving the reflection with the receiving transducer may be referred to as a transmit-receive event. In this way, the time 692 shown in FIG. 6 may be a single transmit receive event with a transmit-receive pair including the same transducer, $612_{(1)}$. Similarly, the time 696 may be a single transmit-receive event with a transmit pair including $612_{(1)}$ and $612_{(3)}$.

Figure 7:
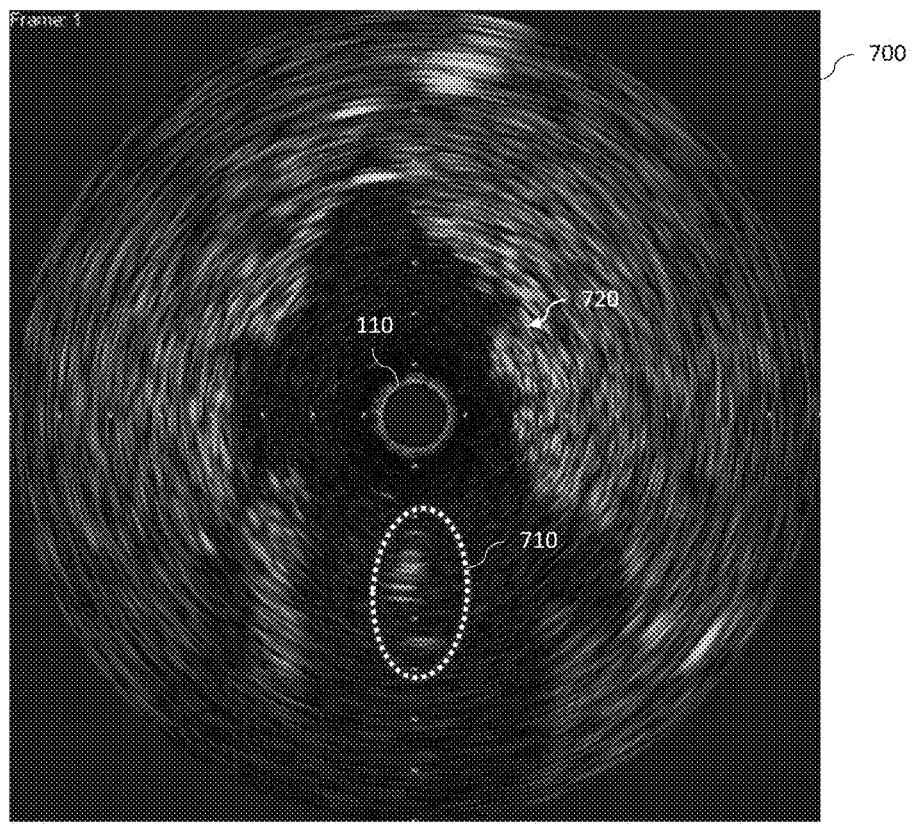
FIG. 7 is a diagrammatic view of an intraluminal ultrasound image with an artifact caused by a high pulse repetition frequency, according to aspects of the present disclosure.

FIG. 7 is a diagrammatic view of an intraluminal ultrasound image 700 with an artifact caused by a high pulse repetition frequency, according to aspects of the present disclosure. FIG. 7 includes a depiction of the ultrasound imaging assembly 110, as well as an artifact 710.

The timing and sequence of transmitting and receiving ultrasound pulses, as described with reference to FIG. 6, can have implications on data collected and the resulting image. For example, the rate at which ultrasound pulses are emitted by the transducers 612 (FIG. 6) can lead to inaccuracies in the ultrasound data and artifacts in the ultrasound images created. The pulse repetition interval (PRI) may refer to the amount of time between emissions of ultrasound pulses. In some embodiments, a PRI for an ultrasound imaging assembly may be any suitable number, such as 1 μs, 10 μs, 100 μs or more, or any suitable number between these values. As the PRI is decreased, there is less time for an emitted pulse to be attenuated before the next pulse is emitted. If the PRI is too low, a receiving transducer may receive ultrasound data from multiple ultrasound pulses, leading to inaccuracies. For example, referring again to FIG. 6, at time 692, transducer $612_{(1)}$ emits a pulse 620 and receives the reflection 630. At time 694, transducer $612_{(1)}$ emits another pulse 622 and transducer $612_{(2)}$ receives reflection 632. If the time between time 692 and 694 is too short, transducer $612_{(2)}$ may receive some ultrasonic energy left over from pulse 620. This leftover energy may be referred to as reverberation. Reverberation from past ultrasound pulses may be effectively attenuated by surrounding tissues or other structures. In some anatomies, however, reverberation may be increased by hard plaque formations or stents in the anatomy.

The effect of receiving transducers receiving reverberation energy from previous pulses is shown in FIG. 7 as artifact 710. Artifact 710 makes it appear to a user of the system 100 as if a structure is present within the lumen 720. When in fact, no such structure is present. The artifact 710 may also be referred to as a false target. As the PM is decreased, artifacts such as artifact 710 in FIG. 7 are more prominent.

Figure 8:
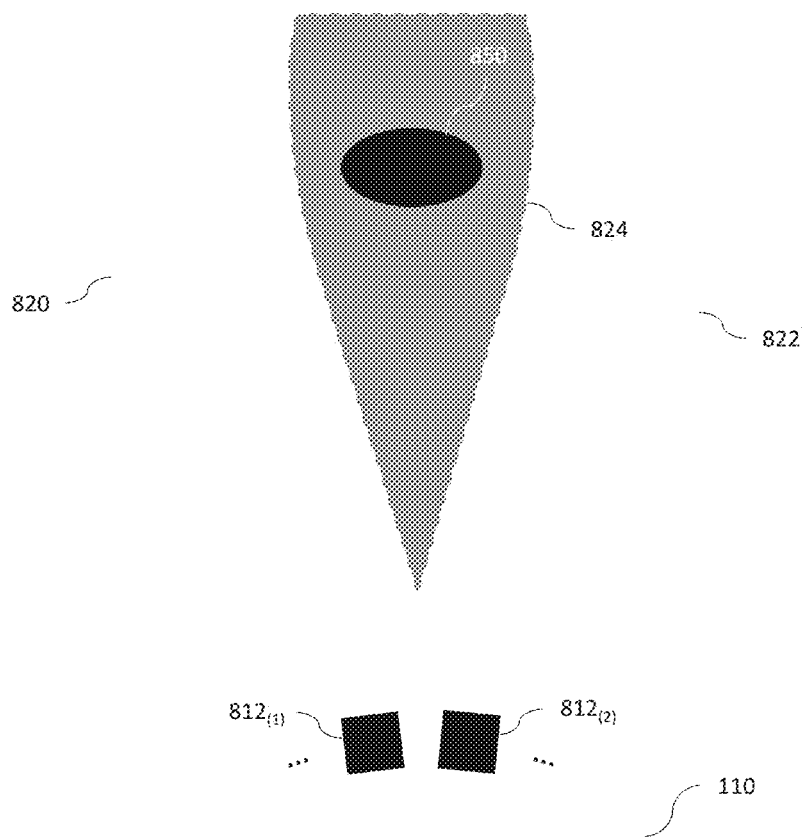
FIG. 8 is a diagrammatic cross-sectional view of transmitting and receiving radiation patterns of ultrasound transducers of the ultrasound imaging assembly, according to aspects of the present disclosure.

FIG. 8 is a diagrammatic cross-sectional view of transmitting and receiving radiation patterns of ultrasound transducers of the ultrasound imaging assembly 110, according to aspects of the present disclosure. FIG. 8 includes a transmitting transducer $812_{(1)}$ and a receiving transducer $812_{(2)}$ with a transmitting radiation pattern 820, a receiving radiation pattern 822, and an overlapping region 824. FIG. 8 also depicts a partial cross-sectional portion of the ultrasound imaging assembly 110 showing two transducers of the circumferential array of transducers.

The circumferential array can include features similar or identical to the array 124 (FIGS. 1 and 2). The circumferential array may include any number of ultrasound transducers, two of which are illustrated in FIG. 8. The ultrasound transducers $812_{(1)}$ and $812_{(2)}$ can include features similar or identical to the transducers 212 of FIGS. 2, 3, and 4. The ultrasound transducers $812_{(1)}$ and $812_{(2)}$ can emit ultrasound pulses and/or receive ultrasound echoes or reflections corresponding to the emitted ultrasound pulses. The ultrasound transducers $812_{(1)}$ and $812_{(2)}$ can be referenced as acoustic elements, transducer elements, or ultrasound transducer elements, or by any other suitable term. The ultrasound transducers $812_{(1)}$ and $812_{(2)}$ can emit an ultrasound pulse in response to an electrical signal that excites the transducers to vibrate. The ultrasound transducers $812_{(1)}$ and $812_{(2)}$ can receive an ultrasound echo by vibrating as a result of incident acoustic energy and converting the received acoustic energy into an electrical signal. The ultrasound transducer $812_{(1)}$ can be a single acoustic element or multiple acoustic elements. Similarly, the ultrasound transducer $812_{(2)}$ can be a single acoustic element or multiple acoustic elements. In embodiments with multiple acoustic elements 812, acoustic elements can be adjacent to one another around the array (e.g., without intervening acoustic elements between the acoustic elements) or can be near or otherwise proximate to one another on the array 505 (e.g., with intervening acoustic elements between the acoustic elements). Each of the acoustic elements of the circumferential array can be oriented differently based on its circumferential position around the array. For example, acoustic element $812_{(1)}$ is oriented differently than the acoustic element $812_{(2)}$. For example, the emitting or outer surfaces of the transducers $812_{(1)}$ and $812_{(2)}$ can be tangential to the surface of the array and/or the surface of the imaging assembly 110 (FIG. 1, 3) at their respective positions. For example, the transducers $812_{(1)}$ and $812_{(2)}$ may emit ultrasound pulses and/or receive ultrasound echoes primarily in a direction perpendicular or normal to the outer surface of the imaging assembly 110.

The radiation pattern 820 of the transducer $812_{(1)}$ can be representative of the direction of acoustic energy (e.g., ultrasound pulses and/or ultrasound echoes) that can be produced or received by the transducer $812_{(1)}$. Similarly, the radiation pattern 822 of the transducer $812_{(2)}$ can be representative of the direction of acoustic energy that can be produced or received by the transducer $812_{(2)}$. The two-dimensional (2D) shape of the radiation patterns 820 and 822 illustrated in FIG. 8 is merely exemplary. The radiation patterns 820 and 822 may extend in three-dimensional (3D) space. In addition, the shape of the radiation patterns 820 and 822 shown in FIG. 8 may be merely exemplary. As previously described, the shape of the radiation patterns 820 and 822 may be determined by various characteristics of the transducers 812, the imaging assembly 110, the emitted or received pulses or reflections, and the surrounding anatomy, etc.

As shown in FIG. 8, the radiation patterns 820 and 822 may overlap in a region 824. The region 824 may be referred to as the combined radiation pattern of the transducers $812_{(1)}$ and $812_{(2)}$. In some embodiments, the transmitting transducer $812_{(1)}$ and the receiving transducer $812_{(2)}$ may be referred to as a transmit-receive aperture. As shown in FIG. 8, the transmit element $812_{(1)}$ may be spaced from the receiving element $812_{(2)}$. Correspondingly, the radiation patterns 820 and 822 are also spaced apart. In some embodiments, transmit element and the receive element can be the same element such that there is no spacing between the transmit and receive elements. In such embodiments, the radiation patterns 820 and 820 may be the same pattern.

In the example shown in FIG. 8, the structure 850 is located in the environment around the IVUS imaging assembly 110. The structure 850 may scatter and/or reflect acoustic energy emitted by the transmit element $812_{(1)}$. The structure 850 may be a structure within the anatomy of a patient, such as a vessel wall, an obstruction, blood, or other structure, or may be any other structure, including synthetic materials such as a stent.

The combined radiation pattern 824 is representative of the region in which a structure may be imaged by the transmitting transducer $812_{(1)}$ and the receiving transducer $812_{(2)}$. In this way, objects within the radiation pattern of a particular transducer may be said to be within the field of view (FOV) of that transducer. An object, such as the structure 850, within the combined radiation pattern 824 of transducers $812_{(1)}$ and $812_{(2)}$ may be within the FOV of these two transducers. As previously mentioned, the field of view for each transducer as defined by its radiation pattern while either transmitting or receiving may define the distance by which a transmitting transducer and receiving transducer may be separated along an array. This distance may then determine how many receiving transducers may be used in conjunction with a single transmitting transducer.

The present disclosure describes systems, devices, and methods that maximize the likelihood that a receiving transducer only receives ultrasound energy corresponding to the transmit-receive event of a given transmit-receive pair and does not receive any reverberation from previous transmit-receive events. This advantageously minimizes reverberation artifacts in the resulting IVUS image, which is an improvement in IVUS image quality and the user's ability to understand the IVUS image and make clinical decisions based on the image.

Figure 9A:
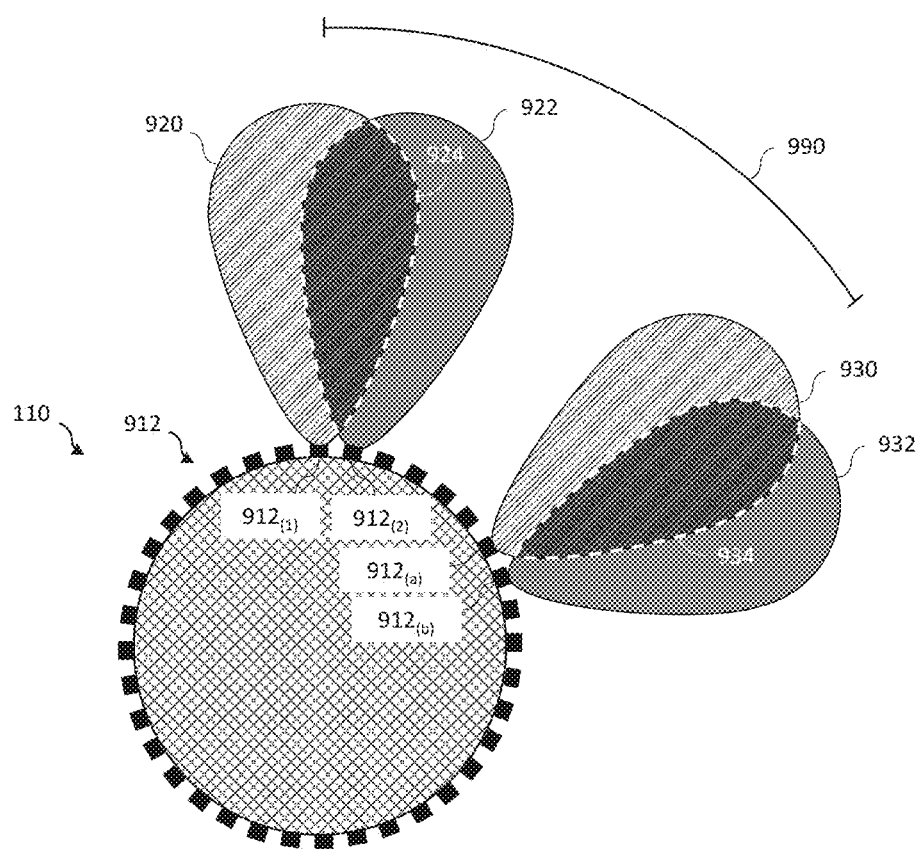
FIG. 9A is a diagrammatic cross-sectional view of transmitting and receiving radiation patterns for two pairs of ultrasound transducers spaced from one another on the ultrasound imaging assembly, according to aspects of the present disclosure.

FIG. 9A is a diagrammatic cross-sectional view of transmitting and receiving radiation patterns for two pairs of ultrasound transducers spaced from one another on the ultrasound imaging assembly, according to aspects of the present disclosure. FIG. 9A may illustrate two separate transmit-receive events. These transmit-receive events may occur at different times or may occur simultaneously.

FIG. 9A illustrates a circumferential array of transducer elements 912 positioned around the exterior of the scanner assembly 110. In some embodiments, the processor circuit may configured to control the circumferential array to emit multiple ultrasound pulses. These ultrasound pulses may include a pulse emitted by the ultrasound transducer $912_{(1)}$ in FIG. 9A. The pulse emitted by the ultrasound transducer $912_{(1)}$ is illustrated by the radiation pattern 920 extending radially outward from the imaging assembly 110. In some embodiments, an ultrasound pulse may be emitted by more than one transducer element. For example, the ultrasound transducers $912_{(1)}$ and $912_{(2)}$ may together form a subset of the circumferential array of ultrasound transducers. This subset may include additional ultrasound transducers. In some embodiments, a subset of ultrasound transducers may include only one transducer. The ultrasound transducers which together form a subset and emit an ultrasound pulse may be positioned adjacent to each other, like the transducers $912_{(1)}$ and $912_{(2)}$, or may be spaced from each other according to any suitable configuration. In some embodiments, the ultrasound transducer(s) which emit(s) an ultrasound pulse may be referred to as an aperture.

At one particular time, the processor circuit 510 (FIG. 5) may be configured to control the circumferential array of transducer elements 912 and cause the transducer $912_{(1)}$ to emit an ultrasound pulse. Immediately after the transducer $912_{(1)}$ has emitted the pulse, the processor circuit may cause the transducer $912_{(1)}$ to receive one or more reflections or echoes associated with the pulse. Both the transmit and receive radiation patterns may be illustrated by the pattern 920 in FIG. 9A.

After the transducer $912_{(1)}$ has transmitted a pulse and received any reflections or echoes, the processor circuit may control the circumferential array and cause a different transducer $912_{(a)}$, or subset of transducers which may include one or more transducers, to emit an additional ultrasound pulse. The transducer $912_{(a)}$ may be any transducer 912 of the circumferential array. In some embodiments, the transducer $912_{(a)}$ is a different transducer from transducer $912_{(1)}$. In some embodiments, the transducer $912_{(a)}$ is spaced from the transducer $912_{(1)}$ by some angle 990. The angle 990 separating transducer $912_{(1)}$ from transducer $912_{(a)}$ may be any suitable angle. The minimum acceptable value of angle 990 may be determined by the processor circuit 510 (FIG. 5) based on the radiation patterns associated with the transducers $912_{(1)}$ and $912_{(a)}$. For example, as shown in FIG. 9A, the radiation pattern 920 may correspond to the transducer $912_{(1)}$ and the radiation pattern 930 may correspond to the transducer $912_{(a)}$. The minimum value of angle 990 may be smallest value at which the radiation patterns 920 and 930 do not overlap. If the angle 990 is chosen such that the radiation patterns 920 and 930 do not overlap, when a pulse is emitted and received first by transducer $912_{(1)}$ in the region of pattern 920 and a second pulse is emitted and received by transducer $912_{(a)}$ in the region of pattern 930 immediately after, any leftover acoustic energy, or reverberation from the first pulse of $912_{(1)}$ is not likely to be received by transducer $912_{(a)}$ because of the physical separation between the transducers.

As described with reference to FIG. 6, emitting and receiving an ultrasound pulse may be performed by two different ultrasound transducers (i.e., a transmit-receive pair). For example, after the transducer $912_{(1)}$ has emitted and received an ultrasound pulse and transducer $912_{(a)}$ has emitted and received an ultrasound pulse, a transmit-receive pair of transducers $912_{(1)}$ and $912_{(2)}$ may transmit and receive an additional pulse. As shown in FIG. 9A, the radiation pattern 920 may correspond to a transmitted pulse from transducer $912_{(1)}$ and the radiation pattern 922 may correspond to a received reflection received by transducer $912_{(2)}$. Combined, these radiation patterns may define the region 924. The transmit receive pair of transducers $912_{(1)}$ and $912_{(2)}$ may, therefore, have a field of view corresponding to this region 924.

After the transmit-receive pair of transducers $912_{(1)}$ and $912_{(2)}$ have completed respectively transmitting and receiving an ultrasound pulse, the transmit-receive pair of transducers $912_{(a)}$ and $912_{(b)}$ may perform a similar transmit-receive event. For example, the radiation pattern 930 may correspond to a transmitted pulse from transducer $912_{(a)}$ and the radiation pattern 932 may correspond to a received reflection received by transducer $912_{(b)}$. Combined, these radiation patterns may define the region 934. The transmit receive pair of transducers $912_{(a)}$ and $912_{(b)}$ may, therefore, have a field of view corresponding to this region 934. In the example described, because the angle 990 is chosen such that the radiation patterns 920, 922, and 924 do not overlap with the patterns 930, 932, and 934, when a pulse is emitted and received first by transducer pair $912_{(1)}$ and $912_{(2)}$ and a second pulse is emitted and received by transducer pair $912_{(a)}$ and $912_{(b)}$ immediately after, any leftover acoustic energy, or reverberation from the first pulse of $912_{(1)}$ is not likely to be received by transducer $912_{(b)}$ because of the physical separation between the transducers. Stated differently, the transducers $912_{(a)}$ and $912_{(b)}$ are out of the field of view (also referred to as a line of sight) of the transducers $912_{(1)}$ and $912_{(2)}$. Similarly, the transducers $912_{(1)}$ and $912_{(2)}$ are out of the line of sight of the transducers $912_{(a)}$ and $912_{(b)}$.

As shown in subsequent figures, the angle 990 may be any suitable angle. As will be discussed in more detail, both the value of the angle 990 and the value of the pulse repetition interval (PRI) (i.e., the time between ultrasound pulses), may be adjusted with differing effects on the amount of unwanted reverberation received by receiving transducers. Adjusting these values may also, then, affect the location and extent of artifacts or false targets in resulting IVUS images.

As described, FIG. 9A illustrates how a processor circuit 510 may control a circumferential array of ultrasound transducers to emit a first ultrasound pulse emitted by a first subset of the circumferential array and a second ultrasound pulse emitted by a second subset of the circumferential array. The first subset of the circumferential array may include one or more ultrasound transducers. The second subset of the circumferential array may include one or more ultrasound transducers. The second subset of the circumferential array may include different ultrasound transducers than the first subset of the circumferential array. The second ultrasound pulse occurs immediately after the first ultrasound pulse in a succession of the multiple ultrasound pulses. The first subset of ultrasound transducers of the circumferential array and the second subset of ultrasound transducers of the circumferential array are circumferentially spaced from one another around the circumferential array and the second subset is outside of a line of sight of first ultrasound echoes associated with the first ultrasound pulse. The processor circuit 510 (FIG. 5) may also be configured to generate an IVUS image based on the ultrasound pulses and output the IVUS image to a display in communication with the processor circuit. In some embodiments, the first the first ultrasound pulse is associated with a first aperture of the circumferential array, and the second ultrasound pulse is associated with a second aperture of the circumferential array. In some embodiments, the processor circuit 510 (FIG. 5) is configured to control the circumferential array to receive the first ultrasound echoes and receive second ultrasound echoes associated with the second ultrasound pulse and generate the IVUS image based on ultrasound data representative of the first ultrasound echoes and the second ultrasound echoes.

In some embodiments, the processor circuit 510 is configured to control the circumferential array to obtain IVUS imaging data. The IVUS imaging data is representative of a first transmit-receive aperture comprising a first combined radiation pattern and associated with at least one first acoustic element of the circumferential array and a second transmit-receive aperture comprising a second combined radiation pattern and associated with at least one second acoustic element of the circumferential array. The IVUS imaging data representative of the second transmit-receive aperture is obtained immediately after the IVUS imaging data representative of the first transmit-receive aperture. In some embodiments, the at least one first acoustic element and the at least one second acoustic element are circumferentially spaced from one another around the circumferential array such that the first combined radiation pattern and the second combined radiation pattern are non-overlapping or minimally overlapping.

Figure 9B:
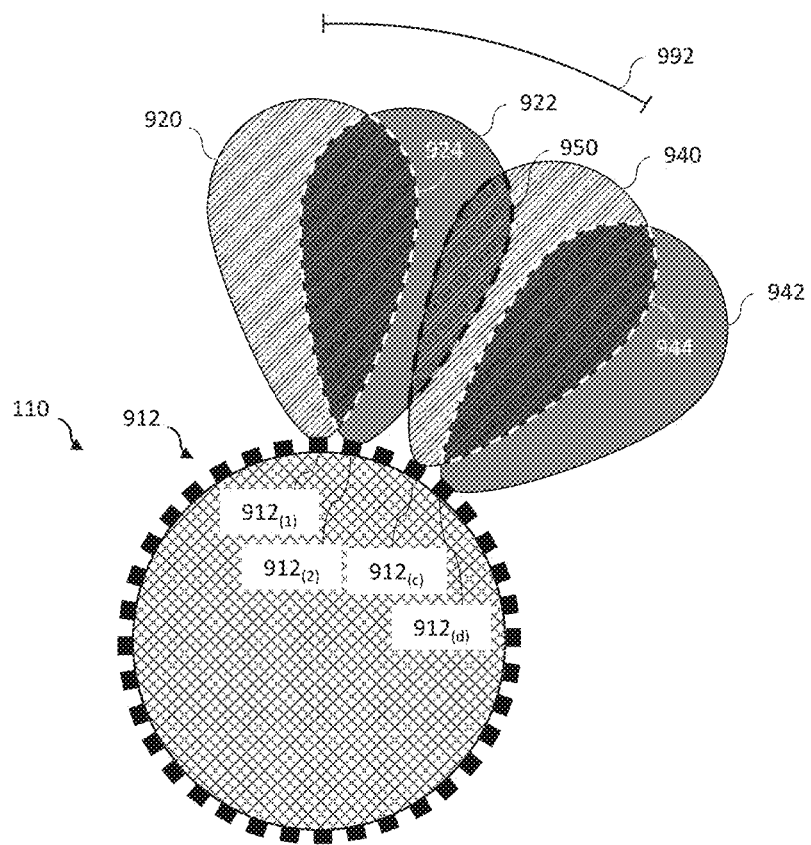
FIG. 9B is a diagrammatic cross-sectional view of transmitting and receiving radiation patterns for two pairs of ultrasound transducers spaced from one another on the ultrasound imaging assembly, according to aspects of the present disclosure.

FIG. 9B is a diagrammatic cross-sectional view of transmitting and receiving radiation patterns for two pairs of ultrasound transducers spaced from one another on the ultrasound imaging assembly, according to aspects of the present disclosure. FIG. 9B may illustrate a sequence of transmitting and receiving ultrasound pulses and reflections, however, the transmit-receive pairs may be spaced from one another by some angle 992 which is smaller than the angle 990 of FIG. 9A, causing the radiation patterns of the transmit-receive pairs to overlap. This overlap 950 may cause reverberations from the first pulse to be received by the receiving transducer associated with the second pulse causing artifacts or false targets.

At one particular time, the transducer $912_{(1)}$ may emit an ultrasound pulse as illustrated by the radiation pattern 920. The transducer $912_{(2)}$ may receive reflections of this first pulse as shown by the radiation pattern 922. Combined, these radiation patterns may define the region 924. The transmit receive pair of transducers $912_{(1)}$ and $912_{(2)}$ may, therefore, have a field of view corresponding to this region 924.

After the transmit-receive pair of transducers $912_{(1)}$ and $912_{(2)}$ have completed respectively transmitting and receiving an ultrasound pulse, the transmit-receive pair of transducers $912_{(c)}$ and $912_{(d)}$ may perform a similar transmit-receive event. For example, the radiation pattern 940 may correspond to a transmitted pulse from transducer $912_{(c)}$ and the radiation pattern 942 may correspond to a received reflection received by transducer $912_{(d)}$. Combined, these radiation patterns may define the region 944. The transmit-receive pair of transducers $912_{(c)}$ and $912_{(d)}$ may, therefore, have a field of view corresponding to this region 944. In the example described, because the angle 992 is chosen such that the radiation patterns 920, 922, and 924 overlap with the patterns 940, 942, and 944, as shown by the region 950, when a pulse is emitted and received first by transducer pair $912_{(1)}$ and $912_{(2)}$ and a second pulse is emitted and received by transducer pair $912_{(c)}$ and $912_{(d)}$ immediately after, some leftover acoustic energy, or reverberation, from the first pulse of $912_{(1)}$ may be received by transducer $912_{(d)}$ because of the smaller physical separation between the transducers. Stated differently, the transducers $912_{(c)}$ and $912_{(d)}$ are within of the field of view (also referred to as a line of sight) of the transducers $912_{(1)}$ and $912_{(2)}$. Similarly, the transducers $912_{(1)}$ and $912_{(2)}$ are within the line of sight of the transducers $912_{(c)}$ and $912_{(d)}$. The example illustrated in FIG. 9B may be one in which the separation angle 992 between the transmit-receive pair $912_{(1)}$ and $912_{(2)}$ and the transmit-receive pair $912_{(c)}$ and $912_{(d)}$ is too small to effectively reduce reverberation. In one exemplary embodiment, the minimum spacing between two consecutively emitting transmit-receive pairs may be 60 degrees. In another exemplary embodiment, the minimum spacing may be 45 degrees. However, the minimum spacing between two consecutively emitting transit-receive pairs may depend on the angular sensitivity of the transducers, the geometry and/or orientation of the transducer elements, the driving frequency of the transmitting pulse, or other factors. At this spacing, the combined radiation patterns of two transmit-receive pairs of transducers is said to be minimally overlapping. In some embodiments, the combined radiation pattern of one transmit-receive pair of transducers and the combined radiation pattern of a second transmit-receive pair of transducers are non-overlapping or minimally overlapping.

In some embodiments, two transmit-receive pairs of ultrasound transducers may be minimally overlapping when the level of reverberation from the first transmit-receive pair and received by the second transmit-receive pair is a certain level below the thermal noise of the ultrasound transducers. For example, in some embodiments, the system 100 or a user of the system 100 may determine that two transmit-receive pairs of transducers are minimally overlapping when reverberation signals between the two are 3 dB below the thermal noise level. The thermal noise level, levels corresponding to emitted pulses and received reflections, and reverberation, may all depend on various aspects of the transducer array, such as the geometry and/or orientation of the array, the size and/or sensitivity of the transducers including the angular sensitivity of the transducers, the frequency of the emitted pulses, the excitation voltage corresponding to the pulse signal, coherence of transmitted and/or received signals, or other factors. In some embodiments, reverberation signals which are beamformed and in the ultrasound range of 62 dB post beamforming will create an artifact in the image. In some embodiments, 62 dB may correspond to a level of speckle noise. However, acquired data before beamforming in IVUS imaging may be in the signal-to-noise ratio range of 26 to 40 dB range above the thermal noise of the transducers.

Figure 9C:
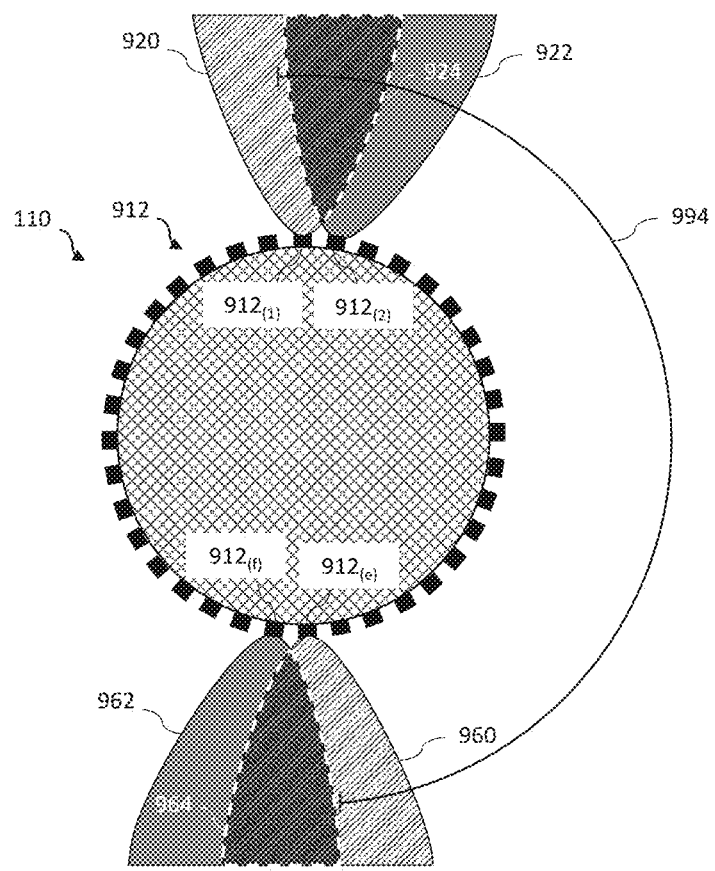
FIG. 9C is a diagrammatic cross-sectional view of transmitting and receiving radiation patterns for two pairs of ultrasound transducers spaced from one another on the ultrasound imaging assembly, according to aspects of the present disclosure.

FIG. 9C is a diagrammatic cross-sectional view of transmitting and receiving radiation patterns for two pairs of ultrasound transducers spaced from one another on the ultrasound imaging assembly, according to aspects of the present disclosure. FIG. 9C may illustrate a sequence of transmitting and receiving ultrasound pulses and reflections, however, the transmit-receive pairs may be spaced from one another by some angle 994 which is larger than the angle 990 of FIG. 9A. This angle 994 may correspond to a 180 degree separation. In other words, the transmit transducer $912_{(1)}$ is on the opposite side of the circumferential array as the transmit transducer $912_{(e)}$.

At one particular time, the transducer $912_{(1)}$ may emit an ultrasound pulse as illustrated by the radiation pattern 920. The transducer $912_{(2)}$ may receive reflections of this first pulse as shown by the radiation pattern 922. Combined, these radiation patterns may define the region 924. The transmit receive pair of transducers $912_{(1)}$ and $912_{(2)}$ may, therefore, have a field of view corresponding to this region 924.

After the transmit-receive pair of transducers $912_{(1)}$ and $912_{(2)}$ have completed respectively transmitting and receiving an ultrasound pulse, the transmit-receive pair of transducers $912_{(e)}$ and $912_{(f)}$ may perform a similar transmit-receive event. For example, the radiation pattern 950 may correspond to a transmitted pulse from transducer $912_{(c)}$ and the radiation pattern 952 may correspond to a received reflection received by transducer $912_{(d)}$. Combined, these radiation patterns may define the region 954. The transmit-receive pair of transducers $912_{(e)}$ and $912_{(f)}$ may, therefore, have a field of view corresponding to this region 954. In the example described, because the angle 994 is creates the maximum spacing between the radiation patterns 920, 922, and 924 and the patterns 960, 962, and 964, when a pulse is emitted and received first by transducer pair $912_{(1)}$ and $912_{(2)}$ and a second pulse is emitted and received by transducer pair $912_{(e)}$ and $912_{(f)}$ immediately after, there is the least likelihood of leftover acoustic energy, or reverberation, being received by transducer $912_{(f)}$.

Figure 10:
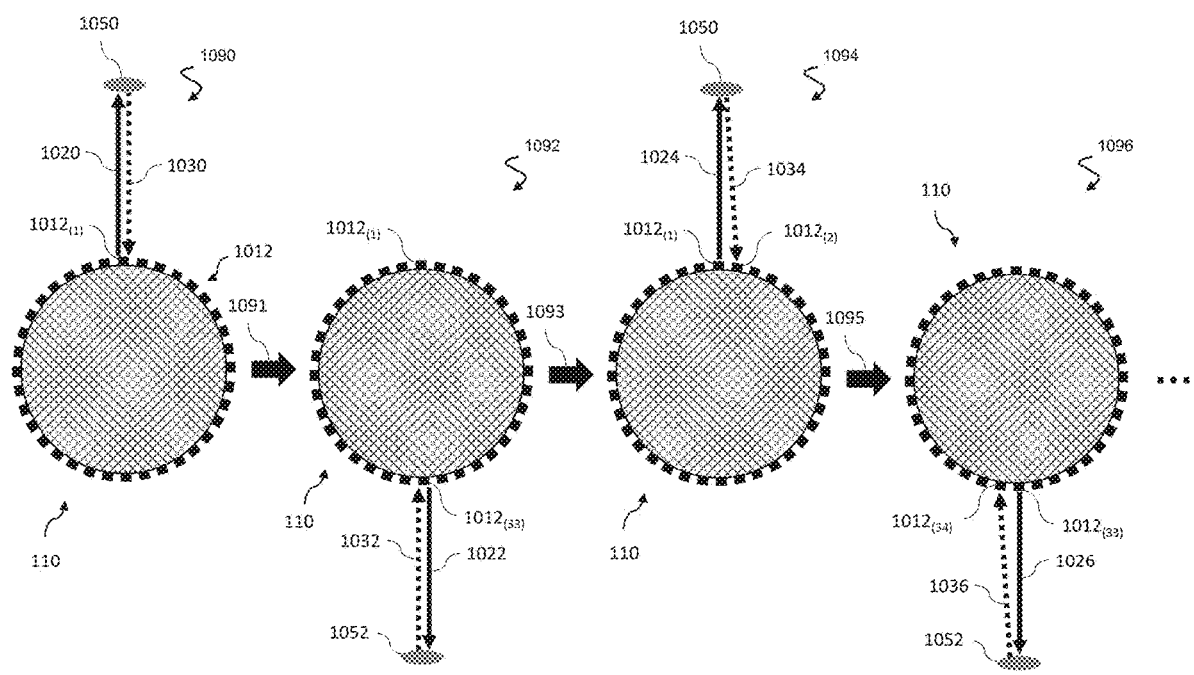
FIG. 10 is a diagrammatic cross-sectional view of the ultrasound imaging assembly illustrating paths of transmitted and received ultrasound pulses over time, according to aspects of the present disclosure.

FIG. 10 is a diagrammatic cross-sectional view of the ultrasound imaging assembly illustrating paths of transmitted and received ultrasound pulses over time, according to aspects of the present disclosure. FIG. 10 may illustrate an exemplary pulse emission sequence.

As shown in FIG. 10, a scanner assembly 110 is illustrated including multiple ultrasound transducers 1012. The transducers 1012 may be substantially similar to any of the other transducers described herein. In the example shown in FIG. 10, the scanner assembly may include 64 ultrasound transducers 1012, though each transducer 1012 may or may not be illustrated in FIG. 10. As previously mentioned, the scanner assembly 110 may include any suitable number of transducers 1012.

At time 1090, the processor circuit 510 (FIG. 5) may cause an ultrasound transducer $1012_{(1)}$ to emit an ultrasound pulse 1020. The ultrasound pulse 1020 may propagate through the surrounding medium and reflect off a structure 1050. This reflection may create a reflection 1030 which propagates back towards the scanner assembly 110. The processor circuit 510 may cause the same transducer $1012_{(1)}$ to receive this reflection 1030.

As shown by the arrow 1091, some amount of time may pass after the ultrasound transducer $1012_{(1)}$ receives the reflection 1030 and before the next transmit-receive event occurs at time 1092. In some embodiments, however, no time may pass between the time ultrasound transducer $1012_{(1)}$ receives reflection 1030, but the transducer $1012_{(33)}$ may emit an ultrasound pulse immediately after the reflection 1030 is received. As previously mentioned, in some embodiments, the transducers $1012_{(1)}$ and $1012_{(33)}$ may be configured to emit ultrasound pulses simultaneously such that time 1090 and 1092 are the same time. In some embodiments, the transducer $1012_{(33)}$ may be configured to emit an ultrasound pulse at some time after the transducer $1012_{(1)}$ emits the pulse 1020 but before it receives the reflection 1030.

At time 1092, a transducer element $1012_{(33)}$ may emit a pulse 1022. The pulse 1022 may propagate radially outward through the surrounding medium and reflect off a structure 1052. This reflection may create a reflection 1032 which propagates back towards the scanner assembly 110. The processor circuit 510 may cause the same transducer $1012_{(33)}$ to receive this reflection 1032.

As shown by the arrow 1093, some amount of time may or may not pass after the ultrasound transducer $1012_{(33)}$ receives the reflection 1032 and before the next transmit-receive event occurs at time 1094.

At time 1094, the transducer element $1012_{(1)}$ may emit a pulse 1024. The pulse 1024 may propagate radially outward through the surrounding medium and reflect off the structure 1050. This reflection may create a reflection 1034 which propagates back towards the scanner assembly 110. The processor circuit 510 may cause a transducer $1012_{(2)}$ to receive this reflection 1034.

As shown by the arrow 1095, some amount of time may or may not pass after the ultrasound transducer $1012_{(2)}$ receives the reflection 1034 and before the next transmit-receive event occurs at time 1096.

At time 1096, the transducer element $1012_{(33)}$ may emit an additional pulse 1026. The pulse 1026 may propagate radially outward through the surrounding medium and reflect off the structure 1052. This reflection may create a reflection 1036 which propagates back towards the scanner assembly 110. The processor circuit 510 may cause a transducer $1012_{(34)}$ to receive this reflection 1036.

This process may continue until all receiving transducers respectively associated with the transmitting transducers $1012_{(1)}$ and $1012_{(33)}$ have received reflections. For example, after the time 1096, the transducer $1012_{(1)}$ may emit an additional pulse and a transducer $1012_{(3)}$ may receive it. Then the transducer $1012_{(33)}$ may emit an additional pulse and a transducer $1012_{(35)}$ may receive it and so on. Then, the transducers $1012_{(2)}$ and $1012_{(34)}$ may serve as the transmitting transducers and the process may continue.

In the example shown in FIG. 10, the ultrasound transducer $1012_{(1)}$ may be referred to as a first subset of the circumferential array. At time 1090, the first subset may emit a pulse and receive reflections of that pulse. The transducer $1012_{(33)}$ may be referred to as a second subset of the circumferential array. At time 1092, the second subset may emit a pulse and receive reflections of that pulse. The transducer $1012_{(2)}$ may be referred to as third subset of the circumferential array. At time 1094, the first subset may emit a pulse and the third subset may receive reflections from that pulse. The transducer $1012_{(34)}$ may be referred to as a fourth subset of the circumferential array. At time 1096, the second subset may emit a pulse and the fourth subset may receive reflections from that pulse. In the example shown, the third subset is within the line of sight of the first ultrasound echoes, and the fourth subset is within the line of sight of the second ultrasound echoes. In some instances, such as at time 1090, the first subset and the third subset are identical. At time 1092, the second subset and the fourth subset may be identical.

In some embodiments, additional repetitive transmit-receive events may be included in the sequence described with reference to FIG. 10. For example, after time 1092, the processor circuit 510 may cause the scanner assembly to repeat the transmit-receive events of time 1090 and 1092. Specifically, after transducer $1012_{(33)}$ has emitted and received a pulse, transducer $1012_{(1)}$ may again transmit and receive a pulse. Then the transducer $1012_{(33)}$ may again transmit and receive a pulse. Similarly, after the time 1096, the transmit-receive events of 1094 and 1096 may be repeated. This process may be referred to as accumulation and may increase the accuracy of ultrasound data received. In some embodiments, the transmit-receive events may be repeated in succession. For example, the transducer $1012_{(1)}$ may emit and receive a pulse two times in succession and then the transducer $1012_{(33)}$ may emit and receive a pulse two times in succession. In other words, the transit-receive event of time 1090 may be completed twice and immediately afterward, the transmit-receive event of 1092 may be completed twice. In this way, the processor circuit 510 may cause the scanner assembly to emit an additional first ultrasound pulse occurring immediately after the first ultrasound pulse in the succession of the plurality of ultrasound pulses and an additional second ultrasound pulse occurring immediately after the additional second ultrasound pulse in the succession of the plurality of ultrasound pulses.

For pedagogical purposes, the sequence of which ultrasound transducers are configured to transmit and which are configured to receive at what times may be described with the following shorthand. An instruction for the first transducer, in FIG. 10 this would be transducer $1012_{(1)}$, to emit an ultrasound pulse may be written as "Tx1." An instruction for the first transducer to receive an ultrasound reflection may be written as "Rx1." An instruction for the second transducer, in FIG. 10 this would be transducer $1012_{(2)}$, to emit an ultrasound pulse may be written as "Tx2" and so forth. A transmit-receive event in which the first transducer is to emit an ultrasound pulse and the second transducer is to receive may be written as "Tx1Rx2." Different transmit-receive events may be separated by an arrow. A written sequence corresponding to that described in FIG. 10 and corresponding to an imaging assembly 110 including 64 transducer elements and spacing different transmit receive pairs by 180 degrees may therefore be as follows:

Tx1Rx1→Tx33Rx33→Tx1Rx2→Tx33Rx34→Tx1-
Rx3→Tx33Rx35→ . . .

After the last receiving transducer associated with the first transmitting transducer has completed receiving reflections, the second transducer may act as the transmitting transducer and the process resumes as follows:

Tx2Rx2→Tx34Rx34→Tx2Rx3→Tx34Rx35→Tx2Rx4→
Tx34Rx36→ . . .

After the last receiving transducer associated with the second transmitting transducer has completed receiving reflections, the third transducer may act as the transmitting transducer and so on until the transmitting transducer 32 and 64 have emitted ultrasound pulses as follows:

Tx32Rx32→Tx64Rx64→Tx32Rx33→Tx64Rx1→Tx32-
Rx34→Tx64Rx2→ . . .

After the last receiving transducer associated with the last transmitting transducer has completed receiving reflections, the ultrasound data acquisition process may be complete.

It is also noted, that any accumulation transmit-receive events may be included in these sequences. For example, a sequence including an accumulation where each transmit-receive event is completed twice may progress as follows:

Tx1Rx1→Tx33Rx33→Tx1Rx1→Tx33Rx33→Tx1Rx2→
Tx33Rx34→ . . .

Alternatively, it may be arranged in this manner:

Tx1Rx1→Tx1Rx1→Tx33Rx33→Tx33Rx33→Tx1Rx2→
Tx1Rx2→ . . .

It is understood that a sequence may include any suitable number of accumulation events and may be organized according to any suitable pattern. For example, a transmit-receive event may be repeated, two, three, four, or more times.

Figure 11A:
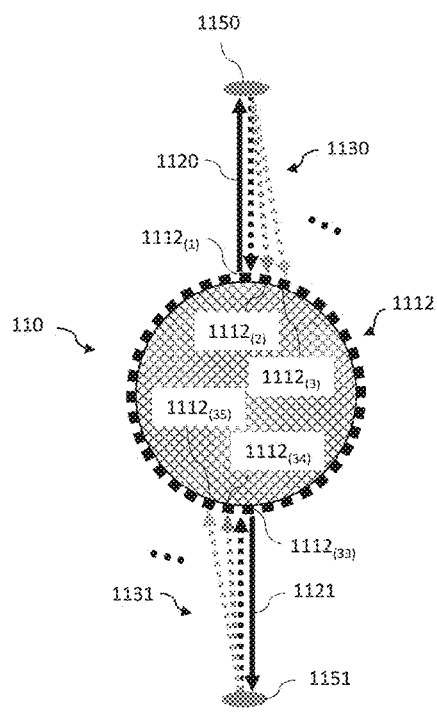
FIG. 11A is a diagrammatic cross-sectional view of the ultrasound imaging assembly illustrating paths of transmitted and received ultrasound pulses, according to aspects of the present disclosure.

FIG. 11A is a diagrammatic cross-sectional view of the ultrasound imaging assembly illustrating paths of transmitted and received ultrasound pulses, according to aspects of the present disclosure. FIGS. 11A through 11D illustrate that a transmit-receive sequence may include more than two transmit-receive pairs with spacing between each pair according to any suitable angle of separation. For example, the sequence pattern shown in FIG. 11A includes two transmit-receive pairs alternating performing transmit-receive events spaced from one another by 180 degrees.

The transmit-receive sequence shown in FIG. 11A may be similar the sequence described with reference to FIG. 10. For example, an ultrasound transducer $1112_{(1)}$ may emit an ultrasound pulse 1120. The same transducer $1112_{(1)}$ may receive a reflection 1130 from the structure 1150. Then, an ultrasound transducer $1112_{(33)}$ may emit an ultrasound pulse 1121. The same transducer $1112_{(33)}$ may receive a reflection 1131 from the structure 1151. The transducer $1112_{(1)}$ may then emit an additional pulse 1120 and the transducer $1112_{(2)}$ may receive a reflection 1130. The transducer $1112_{(33)}$ may then emit an additional pulse 1121 and the transducer $1112_{(34)}$ may receive a reflection 1131 and so on. One embodiment of a sequence shown in FIG. 11A may be written as follows:

Tx1Rx1→Tx33Rx33→Tx1Rx2→Tx33Rx34→Tx1Rx3→
Tx33Rx35→ . . .

Figure 11B:
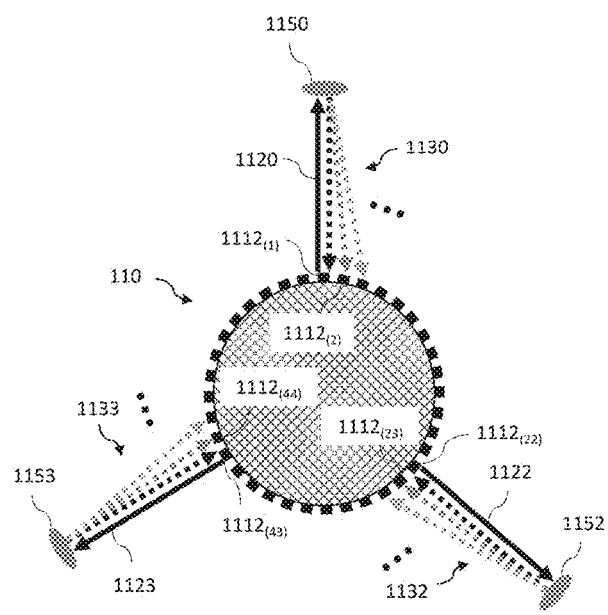
FIG. 11B is a diagrammatic cross-sectional view of the ultrasound imaging assembly illustrating paths of transmitted and received ultrasound pulses, according to aspects of the present disclosure.

FIG. 11B is a diagrammatic cross-sectional view of the ultrasound imaging assembly illustrating paths of transmitted and received ultrasound pulses, according to aspects of the present disclosure. FIG. 11B may illustrate three transmit-receive pairs alternating performing transmit-receive events spaced from one another by 120 degrees.

An ultrasound transducer $1112_{(1)}$ may emit an ultrasound pulse 1120. The same transducer $1112_{(1)}$ may receive a reflection 1130 from the structure 1150. Then, an ultrasound transducer $1112_{(22)}$ may emit an ultrasound pulse 1122. The same transducer $1112_{(22)}$ may receive a reflection 1132 from a structure 1152. Then, an ultrasound transducer $1112_{(43)}$ may emit an ultrasound pulse 1123. The same transducer $1112_{(43)}$ may receive a reflection 1133 from a structure 1153. The transducer $1112_{(1)}$ may then emit an additional pulse 1120 and the transducer $1112_{(2)}$ may receive a reflection 1130. The transducer $1112_{(22)}$ may then emit an additional pulse 1122 and the transducer $1112_{(23)}$ may receive a reflection 1131 and so on. One embodiment of a sequence shown in FIG. 11B may be written as follows:

Tx1Rx1→Tx22Rx22→Tx43Rx43→Tx1Rx2→
    Tx22Rx23→Tx43Rx44→ . . .

Figure 11C:
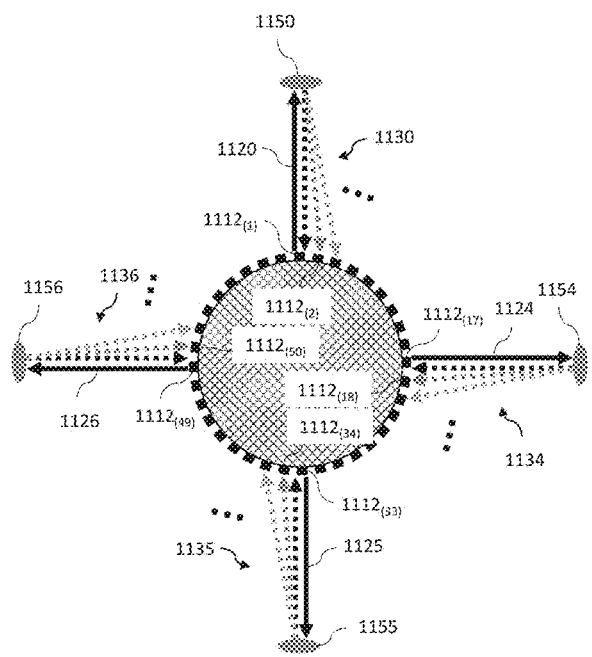
FIG. 11C is a diagrammatic cross-sectional view of the ultrasound imaging assembly illustrating paths of transmitted and received ultrasound pulses, according to aspects of the present disclosure.

FIG. 11C is a diagrammatic cross-sectional view of the ultrasound imaging assembly illustrating paths of transmitted and received ultrasound pulses, according to aspects of the present disclosure. FIG. 11C may illustrate four transmit-receive pairs alternating performing transmit-receive events spaced from one another by 90 degrees.

An ultrasound transducer $1112_{(1)}$ may emit an ultrasound pulse 1120. The same transducer $1112_{(1)}$ may receive a reflection 1130 from the structure 1150. Then, an ultrasound transducer $1112_{(17)}$ may emit an ultrasound pulse 1124. The same transducer $1112_{(17)}$ may receive a reflection 1134 from a structure 1154. Then, an ultrasound transducer $1112_{(33)}$ may emit an ultrasound pulse 1125. The same transducer $1112_{(33)}$ may receive a reflection 1135 from a structure 1155. Then, an ultrasound transducer $1112_{(49)}$ may emit an ultrasound pulse 1126. The same transducer $1112_{(49)}$ may receive a reflection 1136 from a structure 1156. The transducer $1112_{(1)}$ may then emit an additional pulse 1120 and the transducer $1112_{(2)}$ may receive a reflection 1130. The transducer $1112_{(17)}$ may then emit an additional pulse 1122 and the transducer $1112_{(18)}$ may receive a reflection 1134 and so on. One embodiment of a sequence shown in FIG. 11C may be written as follows:

Tx1Rx1→Tx17Rx17→Tx33Rx33→Tx49Rx49→
    Tx1Rx2→Tx17Rx18→Tx33Rx34→
    Tx49Rx50→ . . .

Figure 11D:
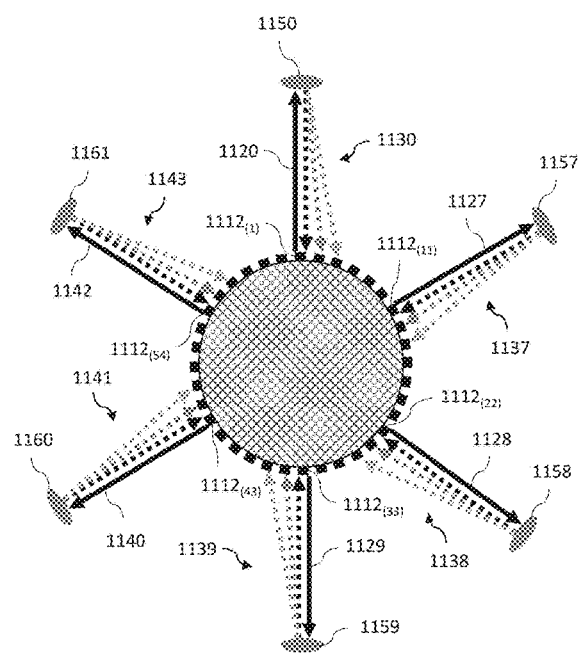
FIG. 11D is a diagrammatic cross-sectional view of the ultrasound imaging assembly illustrating paths of transmitted and received ultrasound pulses, according to aspects of the present disclosure.

FIG. 11D is a diagrammatic cross-sectional view of the ultrasound imaging assembly illustrating paths of transmitted and received ultrasound pulses, according to aspects of the present disclosure. FIG. 11D may illustrate six transmit-receive pairs alternating performing transmit-receive events spaced from one another by 60 degrees.

An ultrasound transducer $1112_{(1)}$ may emit an ultrasound pulse 1120. The same transducer $1112_{(1)}$ may receive a reflection 1130 from the structure 1150. Then, an ultrasound transducer $1112_{(11)}$ may emit an ultrasound pulse 1127. The same transducer $1112_{(11)}$ may receive a reflection 1137 from a structure 1157. Then, an ultrasound transducer $1112_{(22)}$ may emit an ultrasound pulse 1128. The same transducer $1112_{(22)}$ may receive a reflection 1138 from a structure 1158. Then, an ultrasound transducer $1112_{(33)}$ may emit an ultrasound pulse 1129. The same transducer $1112_{(33)}$ may receive a reflection 1139 from a structure 1159. Then, an ultrasound transducer $1112_{(43)}$ may emit an ultrasound pulse 1140. The same transducer $1112_{(43)}$ may receive a reflection 1141 from a structure 1160. Then, an ultrasound transducer $1112_{(54)}$ may emit an ultrasound pulse 1142. The same transducer $1112_{(54)}$ may receive a reflection 1143 from a structure 1161.

The transducer $1112_{(1)}$ may then emit an additional pulse 1120 and the transducer $1112_{(2)}$ may receive a reflection 1130. The transducer $1112_{(11)}$ may then emit an additional pulse 1127 and the transducer $1112_{(12)}$ may receive a reflection 1137 and so on. One embodiment of a sequence shown in FIG. 11D may be written as follows:

Tx1Rx1→Tx11Rx11→Tx22Rx22→Tx33Rx33→
    Tx43Rx43→Tx54Rx54→Tx1Rx2→Tx11Rx12→
    Tx22Rx23→Tx33Rx34→Tx43Rx44→
    Tx54Rx55→ . . .

As shown in FIGS. 11A through 11D, in some embodiments, the transmit-receive pairs may be spaced from one another symmetrically. For example, the processor circuit 510 (FIG. 5) may be configured to control the circumferentially spaced array to cause the first subset and the second subset of ultrasound transducers to be spaced from one another around the circumferential array.

As previously mentioned, in some embodiments, the processor circuit 510 (FIG. 5) may control the circumferentially spaced array in such a way as to cause more than one transmit-receive pair of ultrasound transducers to perform a transmit-receive event simultaneously. For example, the IVUS imaging device may include multiple communication lines in communication with the circumferential array of acoustic elements and the multiple communication lines may include a first data channel and a second data channel. The multiple ultrasound pulses may include a third ultrasound pulse emitted by a third subset of the circumferential array and a fourth ultrasound pulse emitted by a fourth subset of the circumferential array, wherein the processor circuit is configured to control the circumferential array to emit the first ultrasound pulse and the third ultrasound pulse simultaneously. The first ultrasound pulse is associated with the first data channel and the third ultrasound pulse is associated with the second data channel and the processor circuit is configured to control the circumferential array to emit the second ultrasound pulse and the fourth ultrasound pulse simultaneously. The third ultrasound pulse is associated with the first data channel and the fourth ultrasound pulse is associated with the second data channel.

Figure 12A:
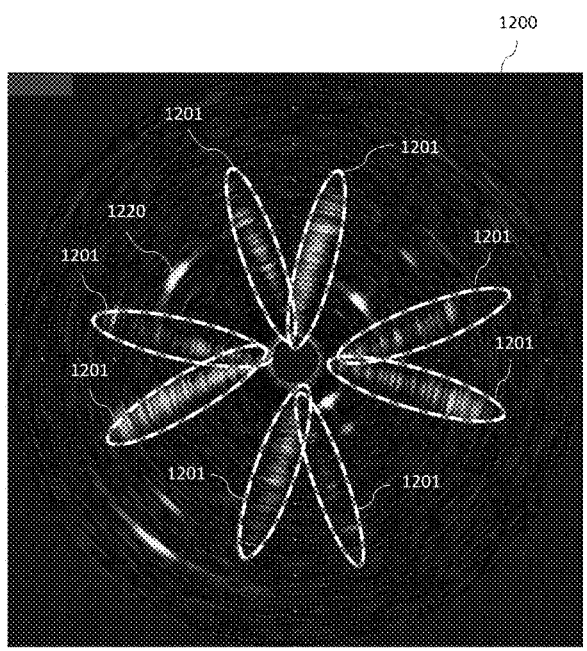
FIG. 12A is a diagrammatic view of an intraluminal ultrasound image with multiple artifacts caused by high pulse repetition frequency, according to aspects of the present disclosure.

FIG. 12A is a diagrammatic view of an intraluminal ultrasound image with multiple artifacts caused by high pulse repetition frequency, according to aspects of the present disclosure. FIG. 12A includes an IVUS image 1200 showing various structures 1220 within the imaged anatomy as well as multiple artifacts 1201.

The presence of artifacts 1201 within the IVUS image 1200 is one example of inaccuracies that may be introduced in the received ultrasound imaging data as a result of reverberation. For example, the methods used to obtain the image 1200 shown in FIG. 12A may be similar to the methods described with reference to FIG. 6. Specifically, when obtaining the ultrasound data corresponding to the image 1200, the processor circuit 510 may have used a sequence of transmitting and receiving ultrasound pulses that included a first transducer emitting a and receiving a pulse and then the same transducer emitting a pulse again instead of alternating transmit-receive events with other different transmit-receive pairs. In addition, a high pulse repetition frequency may have been used to obtain the ultrasound image data corresponding to the IVUS image 1200. As a result, the likelihood of one receiving transducer of receiving reverberation, or unwanted, leftover acoustic energy from a previous ultrasound pulse is higher. Without using multiple transmit-receive pairs of transducers in alternation, the receiving transducers are both spaced closely to one another, and are within one another's field of view or line of sight and, with a high PM, there is not sufficient time for previous ultrasound pulses to attenuate or die out in time for the next ultrasound pulse to be received.

Figure 12B:
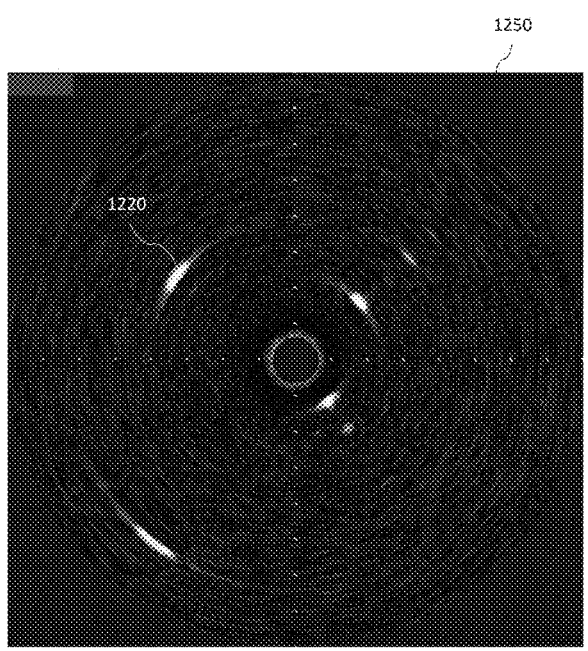
FIG. 12B is a diagrammatic view of an intraluminal ultrasound image obtained using a reverberation signal reduction sequence, according to aspects of the present disclosure.

FIG. 12B is a diagrammatic view of an intraluminal ultrasound image obtained using a reverberation signal reduction sequence, according to aspects of the present disclosure. FIG. 12A includes an IVUS image 1250 showing the same structures 1220 within the imaged anatomy but does not include any artifacts 1201 from reverberation.

The IVUS image 1250 may have been obtained according to the methods of alternating transmit-receive pairs as described in FIGS. 10, and 11A through 11D. By alternating transmit-receive pairs, after one transducer emits an ultrasound pulse and a corresponding transducer receives it, the pulse has more time to attenuate and die out as a different transmit-receive pair of transducers performs a transmit-receive event. In this way, when the original transmit-receive pair emits and receives another ultrasound pulse, there are no left over reverberations from the previous pulse.

Figure 13A:
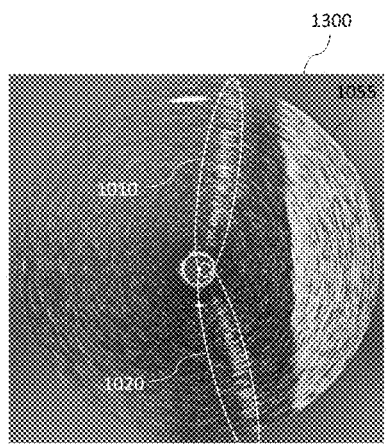
FIG. 13A is a diagrammatic view of an intraluminal ultrasound image with artifacts caused by high pulse repetition frequency, according to aspects of the present disclosure.
Figure 13B:
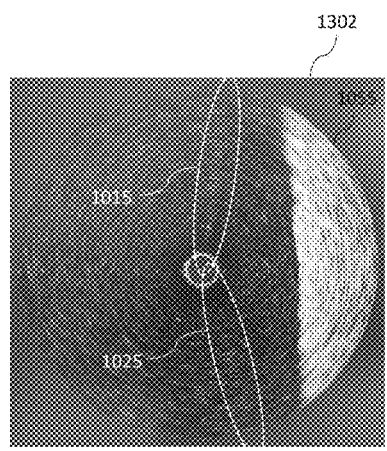
FIG. 13B is a diagrammatic view of an intraluminal ultrasound image obtained using a reverberation signal reduction sequence, according to aspects of the present disclosure.
Figure 13C:
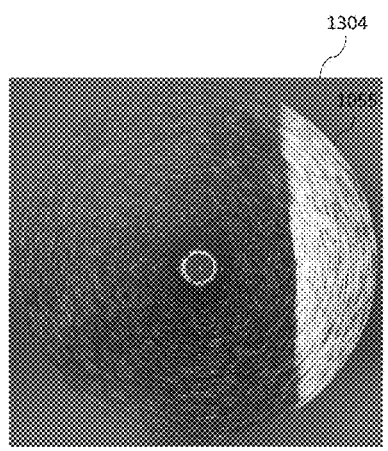
FIG. 13C is a diagrammatic view of an intraluminal ultrasound image obtained using a reverberation signal reduction sequence, according to aspects of the present disclosure.

FIG. 13A is a diagrammatic view of an intraluminal ultrasound image with artifacts caused by high pulse repetition frequency, according to aspects of the present disclosure. Pulse repetition frequency (PRF) may be inversely related to the pulse repetition interval. As PM decreases, PRF increases and vice versa. FIG. 13A will be described in conjunction with both FIG. 13B and FIG. 13C. FIG. 13B is a diagrammatic view of an intraluminal ultrasound image obtained using a reverberation signal reduction sequence, according to aspects of the present disclosure. FIG. 13C is a diagrammatic view of an intraluminal ultrasound image obtained using a reverberation signal reduction sequence, according to aspects of the present disclosure.

In some embodiments, the PRI and spacing between transmit-receive pairs of transducers may be adjusted to provide the clearest image. For example, as the PM for a particular imaging procedure is decreased, the likelihood of reverberation artifacts increases. This is because as the time between ultrasound pulses decreases, there is less time for ultrasound pulses to attenuate before the next pulse is emitted. In addition, as the number of alternating transmit-receive pairs are increased, the likelihood of reverberation artifacts may increase or decrease. For example, if the number of transmit-receive pairs is increased from one to two spaced apart by a 180 degree separation, the likelihood of reverberation artifacts may decrease. This is because, as previously described, there is more time for a pulse from a transmit-receive pair of transducers to attenuate before the same pair is directed to emit another pulse. Similarly, if the number of transmit-receive pairs is increased from one to three spaced by a 120 degree separation, the likelihood of reverberation artifacts may decrease for the same reason. In this case, more time passes after one particular transmit-receive pair emits a pulse before it is directed to emit another pulse. As the number of transmit-receive pairs is continually increased, however, the likelihood of reverberation artifacts may increase if the separation between transmit-receive pairs becomes small enough that the radiation patterns of adjacent transmit-receive pairs begin to overlap. As a result, a user of the system 100 may adjust the number of alternating transmit-receive pairs and the PRI for a particular imaging procedure to minimize the likelihood of reverberation artifacts.

In some embodiments, referring again to FIG. 11D, the processor circuit 510 may alter the sequence of emitted pulses from different transmit-receive pairs of transducers to further decrease the likelihood of reverberation artifacts. For example, the processor circuit 510 may cause the transducers to emit pulses according to a "star" pattern, such that if there are five or more alternating transmit-receive pair of transducers used, after a transmit-receive pair emits a pulse, a pair furthest from that emitting pair will emit a pulse next. In this way, if the spacing between pairs in FIG. 11D is 60 degrees for example, transmit-receive pairs positioned 60 degrees apart next to each other will not emit pulses sequentially. As an exemplary sequence, the processor circuit may direct $1112_{(1)}$ to emit a pulse, then transducer $1112_{(43)}$, then transducer $1112_{(11)}$, then transducer $1112_{(54)}$, then transducer $1112_{(22)}$, then transducer $1112_{(1)}$, then transducer $1112_{(33)}$, then transducer $1112_{(11)}$, and so on. Various other sequences may also be used. By emitting pulses in such a way that neighboring transmit-receive pairs do not emit pulses consecutively, both the benefit of an increased number of transmit-receive pairs (i.e., more time between pulse emissions, or increased effective PM) and the benefit of a decreased number of transmit-receive pairs (i.e., larger effective spacing between transmit-receive pairs) may be realized. This may lead to a decreased likelihood of reverberation artifacts in the resulting IVUS image.

Turning to FIG. 13A, an IVUS image 1300 is presented. FIG. 13A depicts a structure 1055. The structure 1055 may be a vessel wall or some other structure within the surrounding anatomy. FIG. 13A also depicts a reverberation artifact 1010 and a reverberation artifact 1020. The reverberation artifacts 1010 and 1020 may be caused by a low PM or by too small of spacing between consecutively emitting transmit-receive pairs of transducers.

FIG. 13B shows an IVUS image 1302. The IVUS image 1302 depicts the same structure 1055. However, the image 1302 includes two less pronounced reverberation artifacts, namely artifact 1015 and artifact 1025. The IVUS image 1302 may be the result of altering parameters associated with the ultrasound data acquisition. For example, the image 1302 may have been obtained while increasing the PRI. Alternatively, the image 1302 may have been obtained while increasing the spacing between consecutively emitting transmit-receive pairs of transducers. Either of these adjustments may have the effect of decreasing the presence of reverberation artifacts in the resulting IVUS image.

Turning now to FIG. 13C, an IVUS image 1304 is presented. FIG. 13C depicts the same structure 1055 but does not exhibit any reverberation artifacts. This may be a result of further adjustments to the PRI or spacing of emitting transmit-receive pairs of transducers as has been explained.

Figure 14:
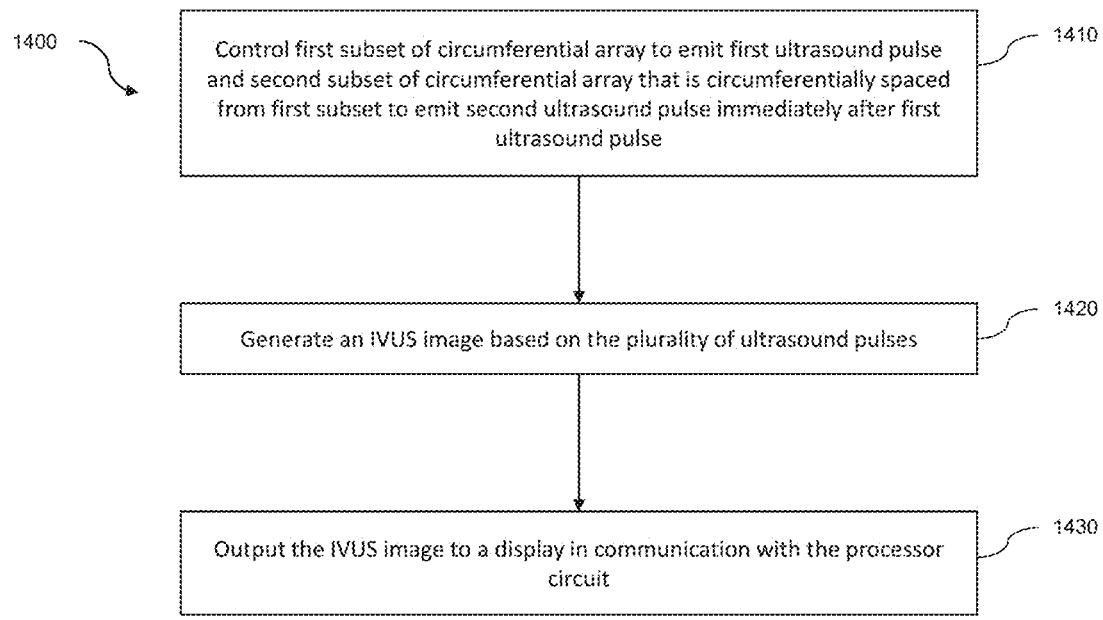
FIG. 14 is a flow diagram for a method for reducing reverberation signals in intravascular ultrasound imaging, according to aspects of the present disclosure.

FIG. 14 is a flow diagram for a method 1400 for reducing reverberation signals in intravascular ultrasound imaging, according to aspects of the present disclosure. As illustrated, the method 1400 includes a number of enumerated steps, but embodiments of the method 1400 may include additional steps before, after, or in between the enumerated steps. In some embodiments, one or more of the enumerated steps may be omitted, performed in a different order, or performed concurrently. The steps of the method 1400 can be carried out by any suitable component within the system 100 and all steps need not be carried out by the same component. In some embodiments, one or more steps of the methods 1400 can be performed by, or at the direction of, a processor circuit of the system 100 (e.g., the processor circuit 510 of FIG. 5), including, e.g., the processor 560 or any other component.

At step 1410, the method 1400 includes controlling the circumferential array to emit a plurality of ultrasound pulses. The plurality of ultrasound pulses includes a first ultrasound pulse and a second ultrasound pulse. Step 1410 includes controlling a first subset of the circumferential array to emit the first ultrasound pulse and controlling a second subset of circumferential array to emit the second ultrasound pulse immediately after the first ultrasound pulse. The second subset of the circumferential array is circumferentially spaced from the first subset of the circumferential array. For example, step 1410 can include controlling the circumferential array to obtain IVUS imaging data. The IVUS imaging data is representative of a first transmit-receive aperture. The first transmit-receive aperture may include a first combined radiation pattern and may be associated with at least one first acoustic element of the circumferential array. IVUS imaging data may also be representative of a second transmit-receive aperture. The second transmit-receive aperture may include a second combined radiation pattern and may be associated with at least one second acoustic element of the circumferential array. The IVUS imaging data representative of the second transmit-receive aperture is obtained immediately after the IVUS imaging data representative of the first transmit-receive aperture. The at least one first acoustic element and the at least one second acoustic element are circumferentially spaced from one another around the circumferential array such that the first combined radiation pattern and the second combined radiation pattern are non-overlapping or minimally overlapping.

At step 1420, the method 1400 includes generating an IVUS image based on the plurality of ultrasound pulses. For example, step 1420 can include generating an IVUS image based on the IVUS imaging data.

At step 1430, the method 1400 includes outputting the IVUS image to a display in communication with the processor circuit. For example, step 1430 can include outputting the IVUS image to a display in communication with the processor circuit.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. An intravascular ultrasound (IVUS) imaging system, comprising:
   an IVUS imaging device configured to be positioned within a blood vessel of a patient, wherein the IVUS imaging device comprises a circumferential array of acoustic elements;
   a processor circuit in communication with the IVUS imaging device, wherein the processor circuit is configured to:
      control the circumferential array to emit a plurality of ultrasound pulses, wherein the plurality of ultrasound pulses comprises:
         a first ultrasound pulse emitted by a first subset of the circumferential array; and
         a second ultrasound pulse emitted by a second subset of the circumferential array,
         wherein the second ultrasound pulse occurs immediately after the first ultrasound pulse in a succession of the plurality of ultrasound pulses,
         wherein the first subset and the second subset are circumferentially spaced from one another around the circumferential array, and
         wherein the second subset is outside of a line of sight of first ultrasound echoes associated with the first ultrasound pulse;
      generate an IVUS image based on the plurality of ultrasound pulses; and
      output the IVUS image to a display in communication with the processor circuit.

2. The system of claim 1,
   wherein the first ultrasound pulse is associated with a first aperture of the circumferential array, and
   wherein the second ultrasound pulse is associated with a second aperture of the circumferential array.

3. The system of claim 1,
   wherein the first subset comprises a single acoustic element of the circumferential array, and
   wherein the second subset comprises a different, single acoustic element of the circumferential array.

4. The system of claim 1,
   wherein the first subset comprises a first plurality of acoustic elements of the circumferential array, and
   wherein the second subset comprises a second plurality of acoustic elements of the circumferential array.

5. The system of claim 1,
   wherein the processor circuit is configured to control the circumferential array to:
      receive the first ultrasound echoes; and
      receive second ultrasound echoes associated with the second ultrasound pulse; and
   wherein the processor circuit is configured to generate the IVUS image based on ultrasound data representative of the first ultrasound echoes and the second ultrasound echoes.

6. The system of claim 5,
   wherein the processor circuit is configured to control the circumferential array to receive the first ultrasound echoes using a third subset of the circumferential array,
   wherein the processor circuit is configured to control the circumferential array to receive the second ultrasound echoes using a fourth subset of the circumferential array,
   wherein the third subset is within the line of sight of the first ultrasound echoes, and
   wherein the fourth subset is within the line of sight of the second ultrasound echoes.

7. The system of claim 6,
   wherein the first subset and the third subset are identical, and
   wherein the second subset and the fourth subset are identical.

8. The system of claim 6,
   wherein the first subset and the second subset are circumferentially spaced from one another by a first portion of the circumferential array,
   wherein the first subset and the third subset are circumferentially spaced from one another by a second portion of the circumferential array that is smaller than the first portion,
   wherein the second subset and the fourth subset are circumferentially spaced from one another by a third portion of the circumferential array that is smaller than the first portion.

9. The system of claim 1, wherein the first subset and the second subset are symmetrically spaced from one another around the circumferential array.

10. The system of claim 1,
wherein the plurality of ultrasound pulses comprises a third ultrasound pulse emitted by a third subset of the circumferential array,
wherein the third ultrasound pulse occurs immediately after the second ultrasound pulse in the succession of the plurality of ultrasound pulses, and
wherein the first subset, the second subset, and the third subset are circumferentially spaced from one another around the circumferential array, and
wherein the third subset is outside of the line of sight of the first ultrasound echoes associated with the first ultrasound pulse and second ultrasound echoes associated with the second ultrasound pulse.

11. The system of claim 10, wherein the first subset and the second subset are symmetrically spaced from one another around the circumferential array.

12. The system of claim 1,
wherein the IVUS imaging device comprises a plurality of communication lines in communication with the circumferential array of acoustic elements,
wherein the plurality of communication lines comprises a first data channel and a second data channel,
wherein the plurality of ultrasound pulses comprises:
a third ultrasound pulse emitted by a third subset of the circumferential array; and
a fourth ultrasound pulse emitted by a fourth subset of the circumferential array,
wherein the processor circuit is configured to control the circumferential array to emit the first ultrasound pulse and the third ultrasound pulse simultaneously,
wherein the first ultrasound pulse is associated with the first data channel and the third ultrasound pulse is associated with the second data channel,
wherein the processor circuit is configured to control the circumferential array to emit the second ultrasound pulse and the fourth ultrasound pulse simultaneously,
wherein the second ultrasound pulse is associated with the first data channel and the fourth ultrasound pulse is associated with the second data channel.

13. The system of claim 1, wherein the plurality of ultrasound pulses comprises:
an additional first ultrasound pulse occurring immediately after the first ultrasound pulse in the succession of the plurality of ultrasound pulses; and
an additional second ultrasound pulse occurring immediately after the second ultrasound pulse in the succession of the plurality of ultrasound pulses.

* * * * *